US012264162B2

(12) United States Patent
Sun et al.

(10) Patent No.: US 12,264,162 B2
(45) Date of Patent: Apr. 1, 2025

(54) COTTON FABRICS CONTAINING POROUS ORGANIC CAGES

(71) Applicant: The Regents of the University of California, Oakland, CA (US)

(72) Inventors: Gang Sun, Davis, CA (US); Peixin Tang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/025,282

(22) PCT Filed: Oct. 22, 2021

(86) PCT No.: PCT/US2021/056168
§ 371 (c)(1),
(2) Date: Mar. 8, 2023

(87) PCT Pub. No.: WO2022/087350
PCT Pub. Date: Apr. 28, 2022

(65) Prior Publication Data
US 2023/0322795 A1    Oct. 12, 2023

Related U.S. Application Data

(60) Provisional application No. 63/104,702, filed on Oct. 23, 2020.

(51) Int. Cl.
*C07D 487/22* (2006.01)
*B01D 53/68* (2006.01)
(Continued)

(52) U.S. Cl.
CPC ......... *C07D 487/22* (2013.01); *B01D 53/685* (2013.01); *B01D 53/70* (2013.01);
(Continued)

(58) Field of Classification Search
CPC .... C07D 487/22; B01D 53/685; B01D 53/68; B01D 53/70; B01D 2257/2062;
(Continued)

(56) References Cited

U.S. PATENT DOCUMENTS

| 2003/0083492 A1 | 5/2003 | Shannon |
| 2015/0173479 A1 | 6/2015 | Adams |
| 2016/0154145 A1 | 6/2016 | Abe et al. |

FOREIGN PATENT DOCUMENTS

| DE | 19947635 A1 * | 1/2001 | ............. A47J 31/08 |
| WO | 2022/087350 A1 | 4/2022 | |

OTHER PUBLICATIONS

Tang, P. et al.; "Fabrication of Robust Functional PolyCationic Nanodots on Surfaces of Nucleophilic Nanofibrous Membrane"; *Appl. Surf. Sci.*; vol. 528; Jun. 9, 2020; p. 146587.
(Continued)

*Primary Examiner* — Camie S Thompson
(74) *Attorney, Agent, or Firm* — Kilpatrick Townsend and Stockton LLP

(57) ABSTRACT

Highly porous nucleophilic organic cages (Nu-POC) were in-situ synthesized on cotton fibers by a condensation reaction between cyanuric chloride and melamine, and the products were employed as a robust wearable and flexible detoxifying protective material (denoted as POCotton) for vaporous pesticides. The covalent growth of Nu-POC particles on surfaces of cotton fibers retained the physical characteristics of Nu-POC to the greatest extend, which include specific surface area and porosity, while the cotton fabrics still remained wearable. The resultant POCotton can repeatedly adsorb fumigant vapors instantly (i.e., equilibrium reached within one minute) and massively (i.e., adsorption capacity at 596.88 mg/g of methyl iodide).

9 Claims, 19 Drawing Sheets

(51) Int. Cl.
  *B01D 53/70* (2006.01)
  *D06M 13/358* (2006.01)
  *D06M 101/06* (2006.01)

(52) U.S. Cl.
  CPC ... *D06M 13/358* (2013.01); *B01D 2257/2062* (2013.01); *B01D 2257/2068* (2013.01); *D06M 2101/06* (2013.01); *D06M 2200/00* (2013.01)

(58) Field of Classification Search
  CPC ........ B01D 2257/2068; D06M 13/358; D06M 2101/06; D06M 2200/00; D06M 101/06
  See application file for complete search history.

(56) References Cited

OTHER PUBLICATIONS

Sun, G.; "Rechargeable Antibacterial N-Halamine Films with Antifouling Function for Food Packaging Applications"; ACS Appl. Mater. Interfaces; vol. 11, No. 19; 2019; pp. 17814-17822.

Huang, C. et al.; "Disinfectant Performance of a Chlorine Regenerable Antibacterial Microfiber Fabric as a Reusable Wiper"; Materials (Basel); vol. 12, No. 1; 2019.

Si, Y. et al.; "Biocidal and Rechargeable N-Halamine Nanofibrous Membranes for Highly Efficient Water Disinfection"; ACS Biomater. Sci. Eng. ; vol. 3, No. 5; 2017; pp. 854-862.

Si, Y. et al.; "Daylight-Driven Rechargeable Antibacterial and Antiviral Nanofibrous Membranes for Bioprotective Applications"; Sci. Adv.; vol. 4, No. 3; 2018.

Liu, N. et al.; "Photo-Induced Self-Cleaning Functions on 2-Anthraquinone Carboxylic Acid Treated Cotton Fabrics"; J. Mater. Chem.; vol. 21, No. 39; Sep. 2011; pp. 15383-15390.

Zhuo, J. et al.; "Antimicrobial Functions on Cellulose Materials Introduced by Anthraquinone Vat Dyes"; ACS Appl. Mater. Interfaces; vol. 5, No. 21; 2013; pp. 10830-10835.

Liu, N. et al.; "Production of Reactive Oxygen Species by Photoactive Anthraquinone Compounds and Their Applications in Wastewater Treatment"; Industrial and Engineering Chemistry Research; Apr. 2011; pp. 5326-5333.

Zhang, Z. et al.; "Daylight-Induced Antibacterial and Antiviral Nanofibrous Membranes Containing Vitamin K Derivatives for Personal Protective Equipment"; Submitted to ACS Appl. Mater. Interfaces; 2020.

Tang, P. et al.; "Generation of Hydroxyl Radicals and Effective Whitening of Cotton Fabrics by H2O2 under UVB Irradiation"; Carbohydr. Polym. ; vol. 160; 2017; pp. 153-162.

Zhang, Z. et al.; "Photoactivities of Vitamin K Derivatives and Potential Applications as Daylight-Activated Antimicrobial Agents"; ACS Sustain. Chem. Eng.; vol. 7, No. 22; 2019; pp. 18493-18504.

International Search Report and Written Opinion in International Application PCT/US2021/056168 mailed Jan. 26, 2022; 6 pages.

Ding, et al.; "Targeted synthesis of a large triazine-based [4+6] organic molecular cage: structure, porosity and gas separation"; *Chem. Commun.*; vol. 51; 2015; pp. 1976-1979.

Hasell, et al.; "Porous organic cages: soluble, modular, molecular pores"; *Nature Reviews Materials*; vol. 1, Article No. 16053; 2016; 26 pages.

Tang, P. et al.; "Wearable super-adsorptive fibrous equipment in situ grafted with porous organic polymers for carcinogenic fumigant defense and detoxification"; *J. Mater. Chem. A*: vol. 8; Oct. 27, 2020; pp. 24128-24136.

\* cited by examiner

COTTON FABRICS CONTAINING POROUS ORGANIC CAGES

CROSS-REFERENCE TO RELATED APPLICATIONS

This application claims priority to U.S. Provisional Patent Application No. 63/104,702, filed Oct. 23, 2020, the contents of which is hereby incorporated by reference in its entirety for all purposes.

BACKGROUND

Methodologies for reducing environmental pollution, occupational, and residential poisoning caused by pesticides and pharmaceuticals have been developed with increased human health concerns.[1-3] Highly porous materials, including activated carbons,[4] metal-organic frameworks (MOFs),[5] covalent organic frameworks (COFs),[6] and porous organic cages (POCs),[7] have been successfully applied in removal of pollutants from the environment. Among them, COFs and POCs are two categories of organic-based porous particles differed in crystallinity, but highly effective in gas separation, gas storage, and nanofiltration.[6,8,9] However, the nature of aforementioned micro- or nanosized particles poses great challenges to their handling, recycling, storage, and transportation in practical applications. To overcome this difficulty, many attempts have been made, such as producing self-standing COF membranes,[10,11] incorporating COFs or POCs onto a continuous substrate,[6,12,13] and weaving flexible COF thread at molecular level.[14] Most of these processes still have to handle small particles.

Fumigants are acutely and chronically toxic chemicals that are widely used in agricultural production, household and post-harvest pest controls.[15] Given the high vapor pressure of fumigants at ambient condition, they can readily evaporate and migrate to the target area as well as release to the atmosphere, posing a risk to farmworkers and residents. Fumigants are mostly colorless and odorless, making them undetectable without sophisticated instruments. Unexpected exposures and death cases have been reported in recent years.[16,17] Although the development of personal protective equipment is urgent in improving protection against occupational and residential exposures to the fumigants, the progress is limited.[18]

Highly porous particles have been introduced to nanofibrous membranes by blending or mixing as functional materials with enhanced flexibility, accessibility, and durability.[19-21] Due to the covering and filling effect that caused by macromolecular polymers, the resultant porous particles-polymer composites usually show significant loss of the desired performance.[10] Cotton fibers are inexpensive and micro-sized cellulosic material widely used in apparel products.[22] The presence of numerous hydroxyl groups in the cellulose fibers allows chemical functionalization reactions feasible and practical.

In view of the foregoing, what is needed in the art are compositions and methods of making highly porous organic particles on flexible, wearable and scalable substrates. The present disclosure satisfies these needs and offers additional advantages as well.

BRIEF SUMMARY

The present disclosure provides an innovative in-situ synthesis method of directly forming highly porous organic particles on flexible, wearable and scalable substrates. Novel cotton fabrics containing highly porous nucleophilic organic cage structures (POCotton) were fabricated and applied for toxic vapor adsorption and detoxification. The introduction of covalently bonded highly porous organic particles on surfaces of traditional textiles provides the development of novel wearable functional materials for personal protective equipment.

As such, in one embodiment, the disclosure provides highly porous nucleophilic organic cages (Nu-POC) in-situ synthesized on cotton cellulose, designed as a wearable and flexible protective material (denoted as POCotton).

In another embodiment, the present disclosure provides a method for detoxifying and or removing fumigant vapors from the environment, the method comprising:

contacting the vapor with a triazine-based nucleophilic porous organic cage grafted on a cotton fiber (POCotton), comprising: a six-membered triazine ring cage grafted to a cotton fiber according to formula I:

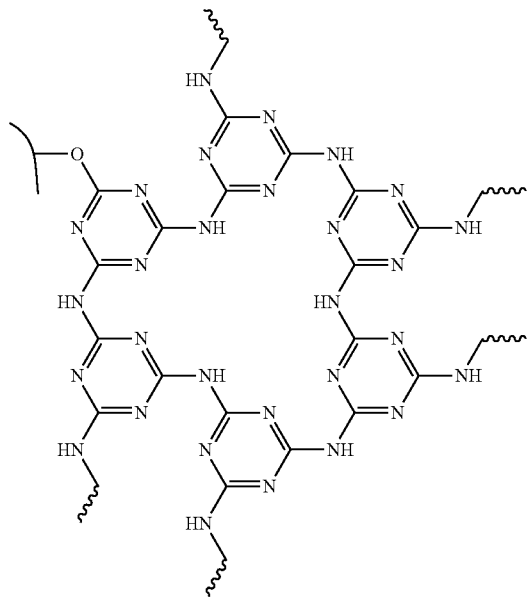

wherein each ⌇ represents attachment to another triazine ring cage, a cotton fiber, $NH_2$ or H; and wherein each ⌇ represents between 0 and 30 triazine ring cages before termination, to allow the detoxification of the fumigant vapor.

In another embodiment, the disclosure provides a triazine-based nucleophilic porous organic cage grafted on a cotton fiber (POCotton), comprising:

a six-membered triazine ring cage grafted to a cotton fiber according to formula I:

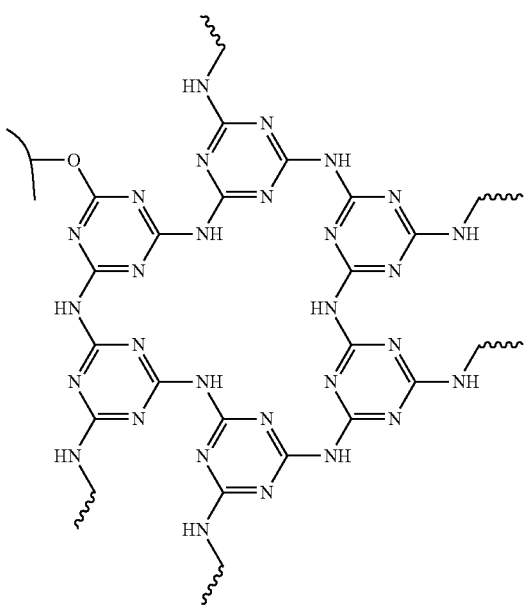

wherein each ⸾ represents attachment to another triazine ring cage, a cotton fiber, or $NH_2$ or H; and wherein each ⸾ represents between 0 and 30 triazine ring cages before termination.

In another embodiment, the disclosure provides a method of making POCotton by a condensation reaction between cyanuric chloride and melamine. The covalent growth of Nu-POC particles on cotton cellulose retain the physical characteristics of Nu-POC to the greatest extent, which includes specific surface area and porosity.

Advantageously, the resultant POCotton can repeatedly remove fumigant vapors rapidly (i.e., equilibrium reached within one minute) and massively (i.e., adsorption capacity at 598 mg/g of methyl iodide). The nitrogen in triazine rings of Nu-POC on POCotton are nucleophilic, allowing the detoxification of sequestered fumigants during long-term storage. A colorimetric signal displays after the detoxification, thus signaling the success of the POCotton function. The success of inducing Nu-POC particles on cotton cellulose without significant loss of Nu-POC performance in terms of rapid fumigant adsorption and detoxification, is useful for POC-based protective materials with the advantages of being flexible, wearable and easy to use.

Various fumigants can be detoxified using the present disclosure. These include, but are not limited to, common fumigants used to treat stored products or nursery stock which include hydrogen cyanide, naphthalene, nicotine, and methyl bromide.

Soil fumigants commonly used as nematocides which include, but are not limited to, methyl iodide, methyl bromide, dichloropropene, propylene oxide, dibromochloropropane, organophosphate insecticides, and chloropicrin.

These and other objects, aspects and embodiments will become more apparent when read with the detailed description and figures that follow.

DETAILED DESCRIPTION

I. Embodiments

Figure 1:
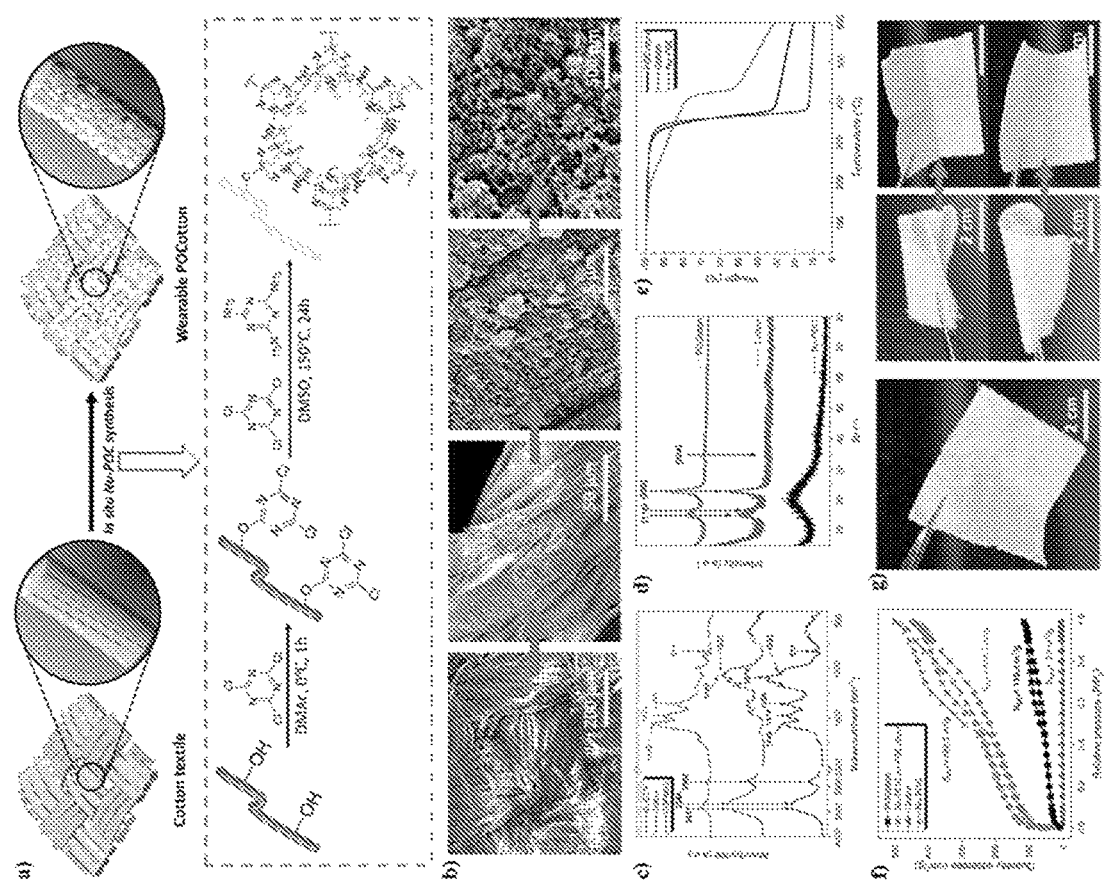
FIG. 1 shows fabrication and characterization of POCotton. a) Schematic illustration of its in-situ synthesis. b) SEM images at enlarged magnifications. c) FTIR spectra. d) PXRD spectra. e) TGA curves. f) $N_2$ adsorption-desorption isotherms. g) Optical images of POCotton that can be folded, rolled up and recovered.

The following description uses cotton as an exemplary fabric. However, a skilled person will understand that the fabric materials include textiles, a fiber, a yarn, a natural or synthetic fabric. In certain instances, the material or fabric is a woven or non-woven fabric with some amount of cellulosic fiber, such as in the form of regenerated cellulose, rayon, cotton fibers or wood pulp fibers. In other aspects, the fibers can be blends of polyester, polyethylene, polypropylene, rayon, acrylics, with natural fibers such as cellulose. In certain aspects, the fabric contains some amount of cellulosic fiber.

In one embodiment, the present disclosure provides a triazine-based nucleophilic porous organic cage grafted on a cotton fiber (POCotton), comprising:
  a six-membered triazine ring cage grafted to a cotton fiber according to formula I:

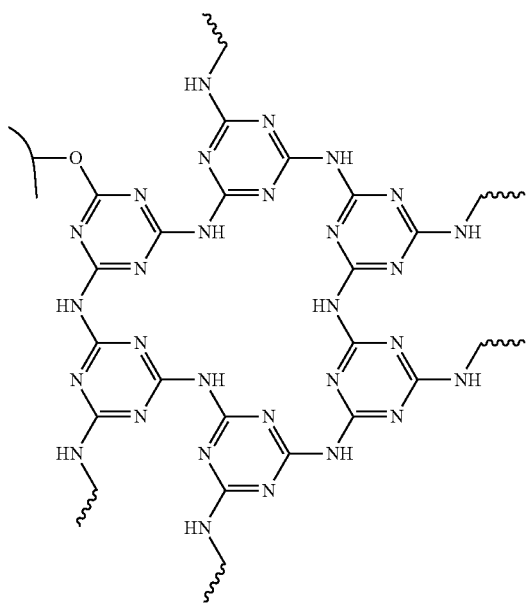

wherein each ⸹ represents attachment to another triazine ring cage, a cotton fiber, $NH_2$, and; wherein each ⸹ represents between 0 and 30 triazine ring cages before termination.

In certain aspects, the triazine rings of the cage can be numbered 1-6 as shown on the attached structure:

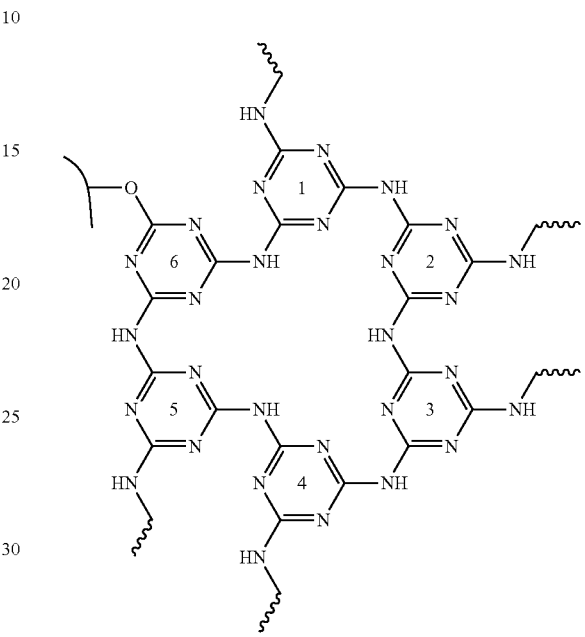

Each of the triazine rings numbered 1-5 is attached to ⸹, which represents another triazine ring cage, a cotton fiber, $NH_2$, or H. In certain instances, the number of triazine ring cages attached to one or more of the rings numbered 1-5 (1, 2, 3, 4, and 5, wherein the first ring is to the right of the fabric attachment) is 0 to 30 such as 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In certain instances, the number of triazine ring cages attached to one or more rings numbered 1-5 is 0-5, or 0-10, or 0-15, or 0-20, or 0-25, or 0-30. In certain instances, the number of triazine ring cages attached to one of more of the rings numbered 1-5 is 1-5, or 1-10, or 1-15, or 1-20, or 1-25 or 1-30.

In certain instances, 0-30 triazine ring cages are attached to one or more of the rings numbered 1-5 (1, 2, 3, 4, and 5) and the terminal triazine is attached to a cotton fiber or terminates as a $NH_2$.

In another embodiment, the present disclosure provides a method for detoxifying and or removing fumigant vapors from the environment, the method comprising:
  contacting the vapor with a triazine-based nucleophilic porous organic cage grafted on a cotton fiber (POCotton), comprising:
    a six-membered triazine ring cage grafted to a cotton fiber according to formula I:

wherein each �663 represents attachment to another triazine ring cage, a cotton fiber, or NH₂ or H; and wherein each �663 represents between 0 and 30 triazine ring cages before termination, to allow the detoxification of the fumigant vapor.

In certain aspects, the fumigant is a member selected from hydrogen cyanide, naphthalene, nicotine, methyl iodide, methyl bromide, dichloropropene, propylene oxide, dibromochloropropane, organophosphate insecticides, and chloropicrin.

In certain aspects, the fumigant is methyl iodide (MeI) or methyl bromide (MeBr). the fumigant is sequestered by the six-membered triazine ring cage grafted to a cotton fiber.

In certain aspects, the fumigant is sequestered by the six-membered triazine ring cage grafted to a cotton fiber with a concomitant color change.

In another embodiment, the present disclosure provides a method of incorporating novel functional agents into POCotton-triazine-based nucleophilic porous organic cage grafted on a cotton fiber, comprising:

providing a six-membered triazine ring cage grafted to a cotton fiber according to formula I:

wherein each �663 represents attachment to another triazine ring cage, a cotton fiber, or NH₂ or H; wherein each �663 represents between 0 and 30 triazine ring cages before termination; and contacting the six-membered triazine ring cage grafted to the cotton fiber with a functional agent to thereby incorporate the functional agent.

In certain aspects, the novel functional agents include photosensitizers, color indicators, and reactive agents.

In certain aspects, the photosensitizers include Rose Bengal, sodium 2-anthroquinone sulfate, anthroquinone-2-carboxylic acid, menadione sodium bisulfite, and riboflavin 5-sulfate.

In certain aspects, the color indicators could be phenol red, phenolphthalein, bromophenol blue, alizarin yellow R, and p-(4-nitrobenzyl)pyridine.

In certain aspects, as demonstrated herein, the disclosure provides a methodology of fabricating wearable POC via in-situ hydrothermal synthesis of a triazine-based nucleophilic POC (Nu-POC) on cotton (denoted as POCotton). Due to the ultrahigh specific surface area and massive porosity of Nu-POC, POCotton is promising to be applied as a novel wearable functional material to provide improved personal protection against fumigant exposure. Moreover, the nucleophilicity of the triazine-based POCotton was investigated to illustrate its detoxification function toward adsorbed fumigants. Not only did POCotton preserve the outstanding functions of the Nu-POC particles in terms of fumigant adsorption and detoxification, but it was also given the advantages of being wearable and flexible, offering potentials for broader applications in personal protections.

In certain aspects, the in-situ synthesis of POCotton involves two steps: 1) activation of cellulose hydroxyls by cyanuric chloride (CCl),[23] and 2) growth of Nu-POC on the activated cellulose via a condensation reaction between the CCl and melamine, as illustrated in FIG. 1a. Although cotton is shown, the fabric or fiber surface in its unmodified state comprises a hydroxyl group. When the hydroxyl group is attached to a carbon atom in the unmodified solid surface, the surface will generally comprise carbohydrates, such as cellulose. The cellulose may, for example, be in the form of bulk cellulose, or in the form of cotton, linen, rayon, or cellulose acetate or other cotton blends. The cotton may, for example, be cotton cloth, cotton gauze or bulk cotton. The carbohydrates may also be in the form of wood or paper.

Figure 5:
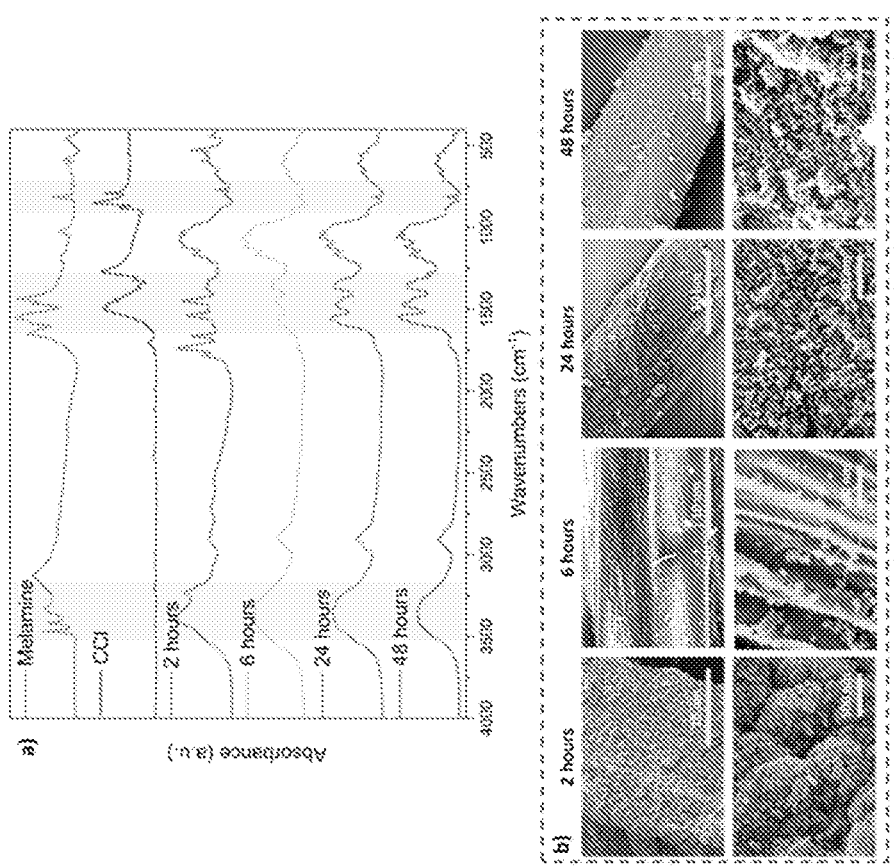
FIG. 5 shows a) FTIR spectra and b) SEM images of POCotton after different durations of in-situ syntheses.

After the in-situ growth of Nu-POC on cotton fibers for 24 hours, the morphology change of the cotton fibers is visible under the SEM (FIG. 1b). Also, FIG. 5 illustrates the morphology and chemical structure change of the POCotton according to reaction time, which confirmed the sufficient synthesis of POCotton at 24 hours. The woven structure of the POCotton was maintained, devoid of any cracks or broken fibers. A significant roughness change appeared on surfaces of the POCotton, revealed by the gradually magnified SEM images of a single fiber of the POCotton (FIGS. 1b-ii and 1b-iii). By further enlarging the view into nanoscale, the surface of each fiber was uniformly covered by mesoporous structures, demonstrating the success of the in-situ synthesis of Nu-POC on cotton cellulose.

Figure 6:
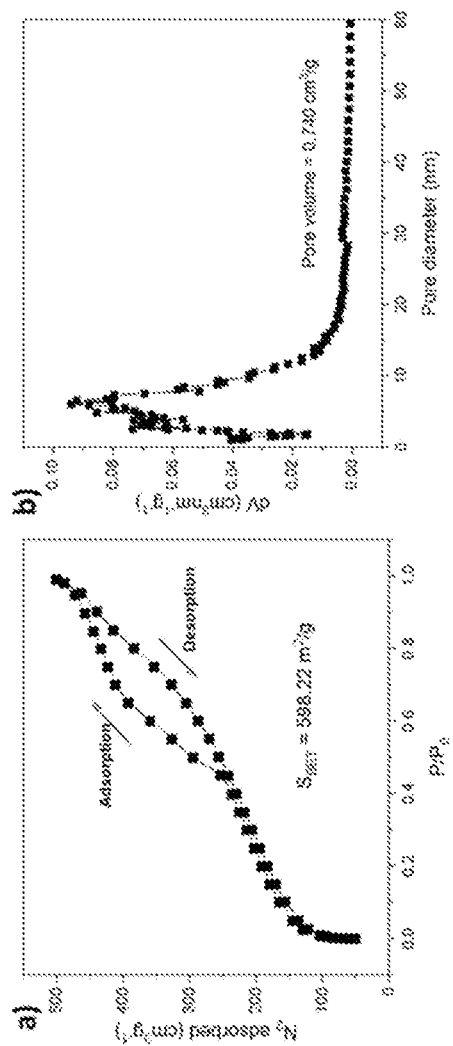
FIG. 6 shows a) $N_2$ adsorption/desorption isotherms of Nu-POC particles performed at 77 K. The BET surface area ($S_{BET}$) was calculated from the $N_2$ adsorption isotherm at 77 K. b) Pore size distribution of Nu-POC particles from 0 to 60 nm.

In certain aspects, to fully understand the function of Nu-POC, the Nu-POC particles were produced according to literature with modifications.[24,25] After heating the deaerated mixture of CCl and melamine at 150° C. for 24 hours, Nu-POC particles in egg-white color were formed with a yield of 79.8%. As presented in FIG. 6, the obtained product showcases high Brunauer-Emmett-Teller (BET) surface area and average pore diameter as 598.2 $m^2/g$ and 6.079 nm, respectively, which are higher than other reported results (Table).[24,25]

TABLE

Physical properties of Nu-POC reported in the literature

| Reference | BET surface area ($m^2/g$)[a] | Pore volume ($m^3/g$) | Pore diameter (nm) |
|---|---|---|---|
| [23] | 93.2 | N/A | N/A |
| [24] | 301.1 | 0.668[b] | 1.41[b] |
| This work | 598.2 | 0.740[a] | 6.079[a] |

[a]Experimental data
[b]Calculated values based on DFT theory

In certain aspects, the pore diameter of a Nu-POC particle is about 2 nm to about 10 nm, such as 1, 2, 3, 4, 5, 6, 7, 8, 9 or about 10 nm. The pore diameter can be about 2-10 nm, about 2-9 nm, about 3-8 nm or about 3-8 nm.

In certain aspects, the surface area of Nu-POC is about 400 $m^2/g$ to about 1000 $m^2/g$, or 400 $m^2/g$ to about 900 $m^2/g$, or 400 $m^2/g$ to about 800 $m^2/g$, or about 400 $m^2/g$ to about 600 $m^2/g$.

Figure 7:
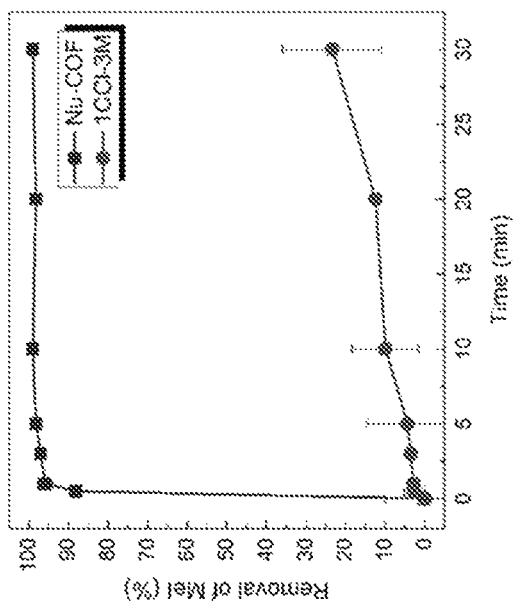
FIG. 7 shows results of MeI (456 μg/mL: 98%×1 μL) removal by Nu-POC particles and 1CCl-3M particles.

The resultant Nu-POC particles (25 mg) could instantly remove 98.99% of 456 μg/mL methyl iodide (MeI), a fumigant representative, within 1 minute (FIG. 7). To clarify the essential role of the porosity of the Nu-POC, another non-porous particle was synthesized by controlling both of the molar ratio of CCl:melamine=1:3 and temperature (see details below).

Scheme. Synthesis of non-porous 1CCl-3M from CCl and melamine.

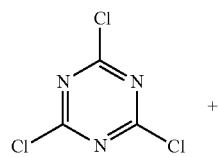

+

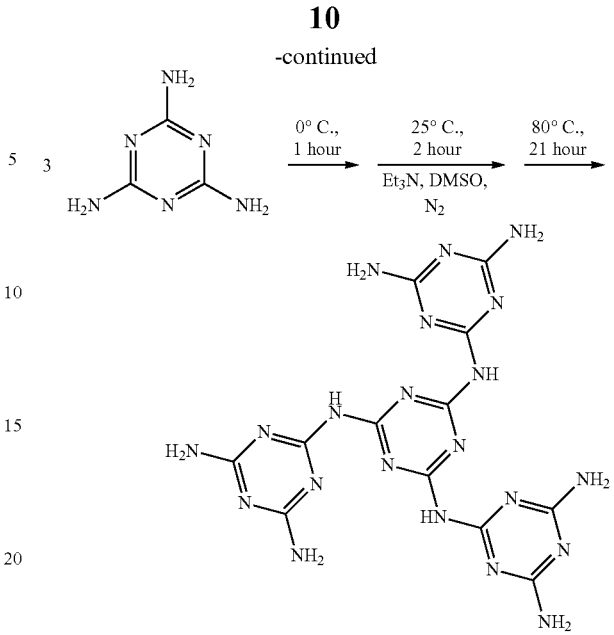

The non-porous particles (named as 1CCl-3M) displayed limited fumigant removal efficacy, only 23.36% of MeI was removed from the headspace in the incubation system for 30 minutes. Here, the decrease of MeI can be explained as the slow detoxification of MeI by the nucleophilic nitrogen in triazine rings (triazine-N) and primary amines in the 1CCl-3M structure. The difference of porosity between Nu-POC and 1CCl-3M was also investigated from a water regain test. The weight of the Nu-POC increased by 750.67% after dispersing in deionized water for 1 hour, whereas only 40% weight add-on was noticed for 1CCl-3M after water filling.

Figure 8:
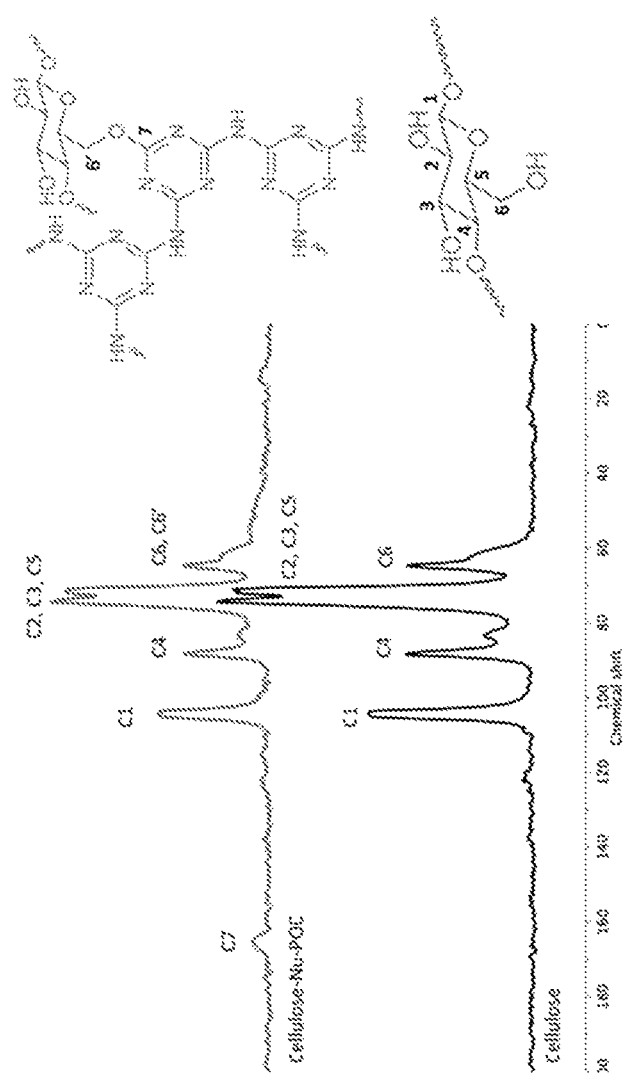
FIG. 8 shows solid phase $^{13}C$ CP/MAS NMR of POCotton and cotton.

In certain aspects, the conditions of the in-situ synthesis including deaerating the reaction system with $N_2$, keeping the stirring rate at 500 rpm, and adding triethylamine ($Et_3N$) as a catalyst, were controlled to optimize the production of POCotton. As a result, the grafting ratio of Nu-POC on cotton fibers reached to 26.21% based on the weight increase. In FIG. 1c, the FTIR spectrum of the POCotton shows a combination of characteristic peaks of cotton and the Nu-POC particles with some peak shifts. The peaks at 1548 $cm^{-1}$, 1474 $cm^{-1}$, and 1354 $cm^{-1}$ in both the Nu-POC and the POCotton spectra represent the triazine rings. The breathing mode of the triazine ring was also shown as a sharp peak at 813 $cm^{-1}$.[26] The covalent linkage between the Nu-POC and the hydroxyls of cellulose was confirmed by the peak intensity decrease at 1033 $cm^{-1}$, which referred to the consumption of hydroxyl groups in cellulose by forming ether bonds with the Nu-POC. Moreover, a peak shift from 1060 $cm^{-1}$ to 1078 $cm^{-1}$ in the POCotton spectrum illustrated the domination of aromatic ethers over the aliphatic ethers in the POCotton structure, which proved the C—O—C bond formation between cellulose hydroxyls and the triazine ring.[26] The presence of the Nu-POC on the POCotton can be further examined through solid phase $^{13}C$ coupling polarization/magic angle spinning (CP/MAS) NMR spectra (FIG. 8). Characterized by powder X-ray diffraction (PXRD), the Nu-POC mostly presents amorphous arrangement by showing a broad peak at 2θ=20°, which refers to the (220) plane of its alignment but with very low crystallinity (FIG. 1d).[27] In addition, the POCotton showcases no effect on the crystallinity of the cotton fibers, whose crystal planes are labeled in FIG. 1d in black.[28] Upon a heat treatment, the Nu-POC particle shows an early weight loss but higher decomposition temperature at around 450° C. among cotton and the POCotton (FIG. 1e). The POCotton displays similar decomposition pattern as cotton fibers, but more residues upon heating to 600° C. The increase of 11.05% of the residues from the POCotton represents the addition of nitrogen- and carbon-enriched moieties to the cotton fibers.

In certain aspects, the nitrogen atoms in the triazine rings of Nu-POC on POCotton are nucleophilic and detoxify sequestered fumigants during long-term uses and storage. In one aspect, a colorimetric signal can reveal failure of the functions due to the detoxification of the agents and formation of a conjugated structure of Nu-POC. The success of inducing Nu-POC particles on cotton fibers without significant loss of Nu-POC performance in terms of rapid fumigant adsorption and detoxification, is quite advantageous. The POC-based protective materials have the advantages of being flexible, wearable and easily processible.

The disclosure provides fumigant removal efficacy of the Nu-POC once grafted on cotton fibers. As the $N_2$ adsorption-desorption isotherms show in FIG. 1f, both the Nu-POC and the POCotton show type IV adsorption isotherm with hysteresis under high partial pressure ($P/P_0$=0.4-1.0). It can thus be concluded that the rapid fumigant removal by the Nu-POC is driven by capillary condensation, a process that vaporous chemicals are adsorbed and condensed to become liquid in porous materials, which supports the observation of polydisperse mesoporous characteristics of both the Nu-POC and the POCotton. The cotton fibers have a limited BET surface area ($S_{BET}$=2.9 m$^2$/g), and the $S_{BET}$ of the POCotton was examined as 110.3 m$^2$/g. However, by considering the actual amount of the Nu-POC on surfaces of the POCotton (i.e., the grafting ratio=26.21%), the $S_{BET}$ (424.2 m$^2$/g) and pore volume (0.662 cm$^3$/g) of the Nu-POC on the fibers are comparable with that of the particles. This is a good achievement on preparation of wearable Nu-POC materials (i.e., POCotton) via the in-situ synthesis without significantly affecting the nature of the Nu-POC.

Figure 9:
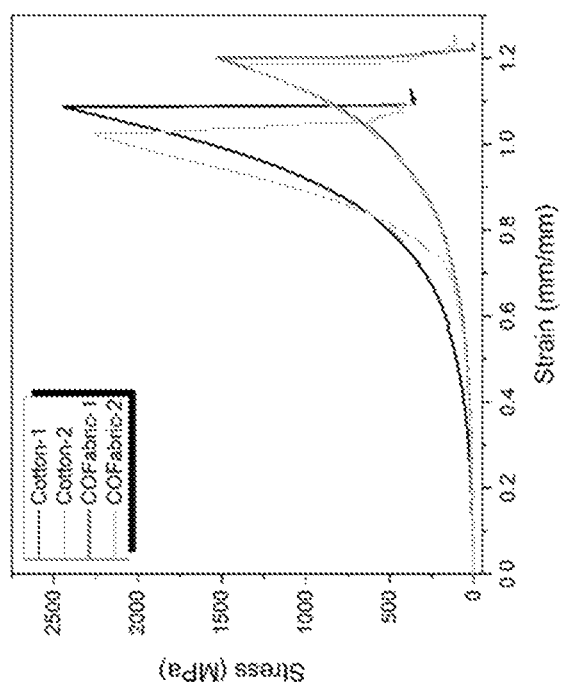
FIG. 9 shows the stress-strain curve of cotton and POCotton.

In certain aspects, although the tensile strength of the resultant POCotton decreased by around 40% after a high-temperature treatment (FIG. 9), whose tensile stress-at-break is still thousand times higher than many flexible protective materials made of nanofibers,[29,30] ensuring the wear ability and serviceability of the POCotton in real applications. Meanwhile, the air permeability of the POCotton (222.0 ft$^3$/ft$^2$) only showed limited decrease compared with the pristine cotton (382.2 ft$^3$/ft$^2$), retaining the breathability of the products. In addition, the POCotton is flexible as traditional textiles, with the ability to be folded, rolled-up, and recovered (FIG. 1g), allowing its broad applications in developing personal protective equipment, functional household apparels, and smart textiles.

Figure 2:
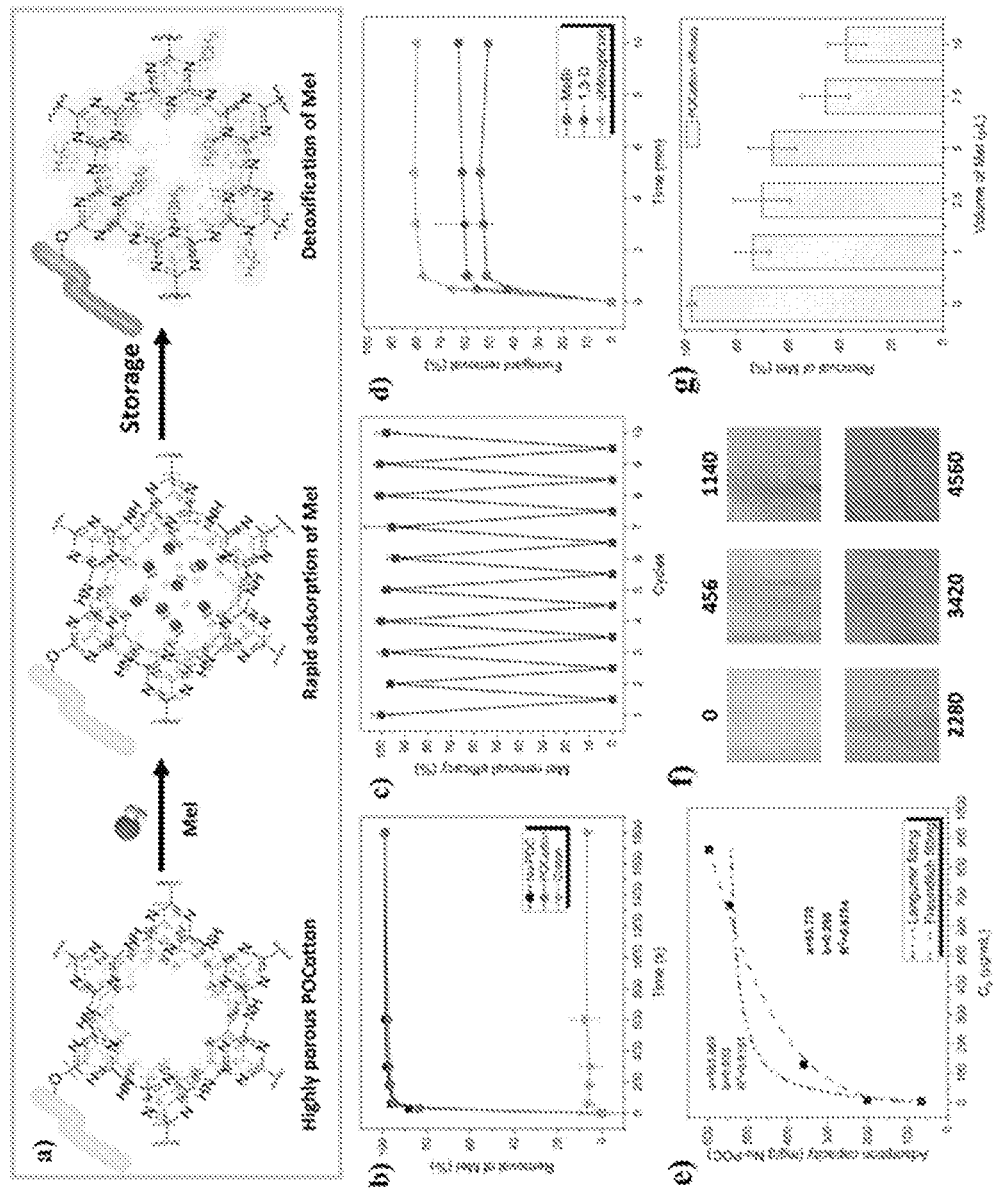
FIG. 2 shows demonstration of fumigant adsorption and detoxification functions of POCotton: a) Adsorption and detoxification mechanisms. b) Methyl iodide (456 μg/mL) adsorption according to time. c) MeI (456 μg/mL) adsorption under repeating exposure challenges. Each cycle of the challenge was performed with alternative 5 min MeI exposure and 10 min low-pressure venting. d) Adsorption functions toward other fumigants. e) Adsorption isotherms and capacity of MeI. f) Optical images of POCotton after different amounts of MeI adsorption and detoxification. The numbers labeled in the figure refer to the initial concentration (μg/mL) of MeI during the challenges. g) Adsorption efficacy retain after different degrees of challenges with MeI.

In certain aspects, the specific surface area and the porosity of the POCotton may relate to fumigant adsorption, and the enrichment of nucleophilic triazine-N in the Nu-POC is expected to have an ability of detoxifying adsorbed alkylating fumigants through a nucleophilic substitution reaction (FIG. 2a). To prove the proposed functions, 100 mg POCotton (i.e., contains ~25 mg Nu-POC particles) was first challenged with 456 μg/mL of MeI at room temperature. In FIG. 2b, a time-dependent MeI adsorption curve of the POCotton overlapped with that of the Nu-POC particles (25 mg), and both achieved the equilibrium within 1 minute with a high removal efficiency of >98%. Excitingly, 30-seconds of adsorption already showed more than 80% of MeI uptake by both the POCotton and the Nu-POC of their equilibrium capacities. However, the pristine cotton presents no effect on MeI adsorption (FIG. 2b).

Figure 10:
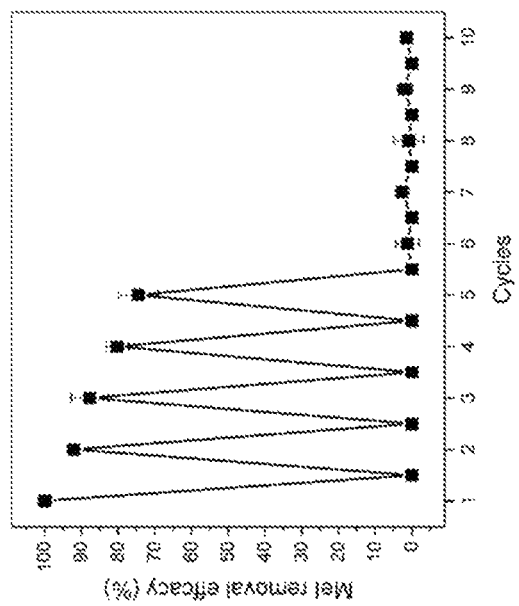
FIG. 10 shows fumigant adsorption efficiency of POCotton with repeated challenges by MeI (456 μg/mL: 98%×1 μL) without regeneration. The MeI adsorption time was 5 min in each cycle.
Figure 11:
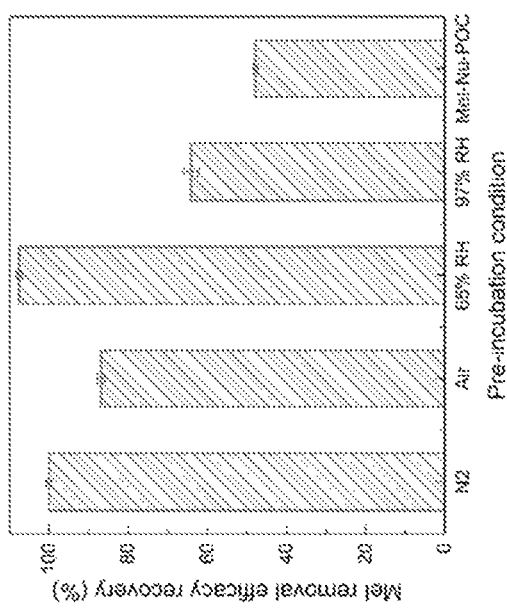
FIG. 11 shows MeI adsorption efficacy recovery of POCotton that has been pre-incubated under $N_2$, air, and moisture conditions for 24 hours. The label of MeI-Nu-POC means the sample was pre-treated by 6840 μg/mL of MeI (98%×15 μL) and stored for 24 hours before testing.

In certain aspects, at least 10 cycles of highly efficient MeI adsorption by the POCotton were achieved, as shown in FIG. 2c. After MeI exposure (5 min), the POCotton was treated under vacuum (i.e., regeneration process) (10 min) to release the adsorbed fumigants in the mesopores of the POCotton for the next round of fumigant challenge. The MeI adsorption efficiency in each cycle was compared with that of a virgin POCotton. However, if the regeneration was not processed, the adsorption efficiency gradually decreased in the first five cycles and completely lost upon further challenges (FIG. 10), which is due to the complete occupation of the mesopores in the POCotton by MeI. The POCotton also presents excellent adsorption performance toward other commonly used fumigants, including methyl bromide (MeBr), 1,3-dichloropropene (1,3-D), and chloropicrin. In FIG. 2d, the removal equilibrium of these fumigants was achieved rapidly (i.e., within 1 minute) by showing similar time-dependent curves to that of MeI. Because of the presence of methanol as the solvent of above fumigants, most of the pore volumes could be competitively occupied by methanol, resulting in a relatively low removal capacity of these three fumigants (FIG. 2d). Here, the removal capacities are correlated to the injected volume of each fumigant, which was determined by the initial concentrations of the fumigants provided by venders. Fortunately, the mesopores in the POCotton will not be persistently occupied by $N_2$, air, nor by moisture (65% relative humidity (RH)) (FIG. 11), which commonly exist in the environment. Once the RH reached 97%, however, only 64.1% of the efficacy was retained on the POCotton (FIG. 11).

Figure 12:
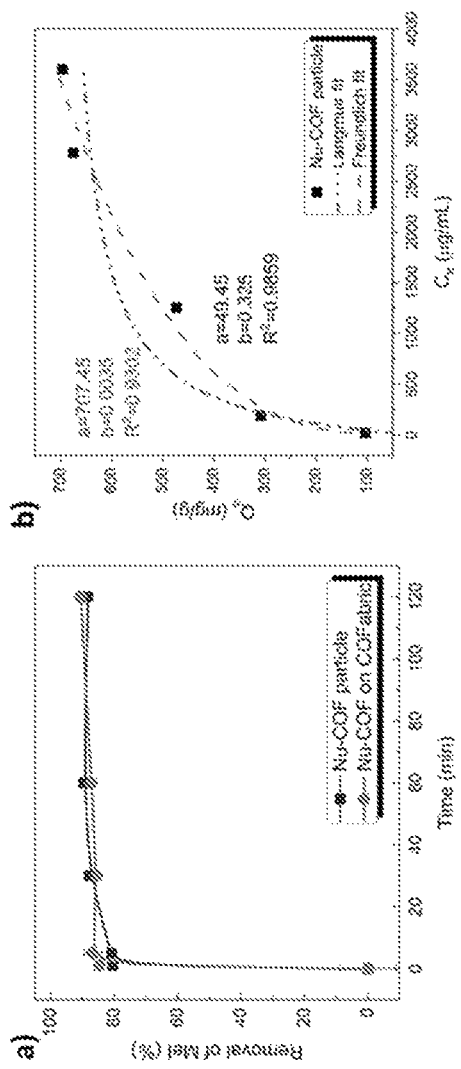
FIG. 12 shows a) High amounts of MeI (2280 μg/mL: 98% MeI×5 μL) adsorption by Nu-POC particles and POCotton according to adsorption time. b) Adsorption capacity of Nu-POC particles.

In certain aspects, the capacity of fumigant removal was further studied by challenging the POCotton with 98% MeI (the injected volumes were varied from 1 μL to 10 μL), and the results were compared with that of the Nu-POC particles. Although the adsorption equilibrium for the POCotton reached within five minutes (taking 5 μL of 98% MeI as an example) (FIG. 12a), the MeI adsorption capacities on the POCotton was investigated upon a 1-hour duration to ensure the achievement of the adsorption equilibrium under all MeI concentrations. The adsorption of MeI on the POCotton fits better with the Freundlich isotherm ($R^2$=0.9754) (FIG. 2e), and the maximum removal capacity was obtained experimentally as 596.88 mg/g of the Nu-POC, slightly lower than that of the Nu-POC particles (695.95 mg/g of Nu-POC) (FIG. 12b). Under a short treatment (i.e., <1 hour), the physical adsorption of fumigants is the key mechanism of protection provided by the POCotton.

Figure 13:
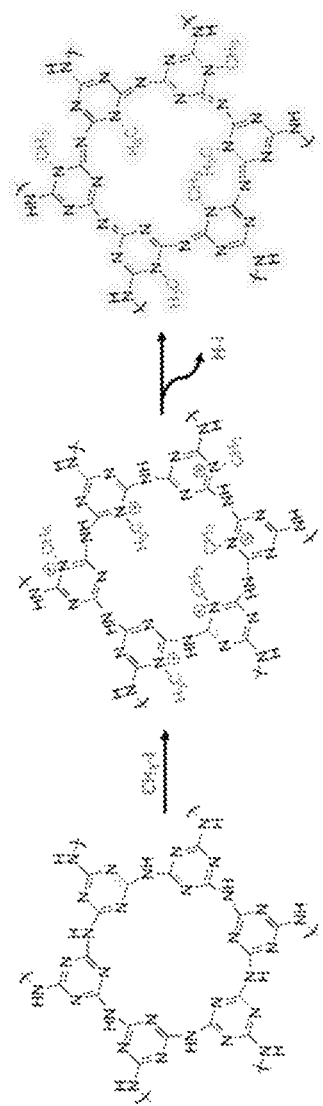
FIG. 13 shows a reaction mechanism between Nu-POC and MeI, resulting in MeI detoxification and Nu-POC color change.
Figure 14:
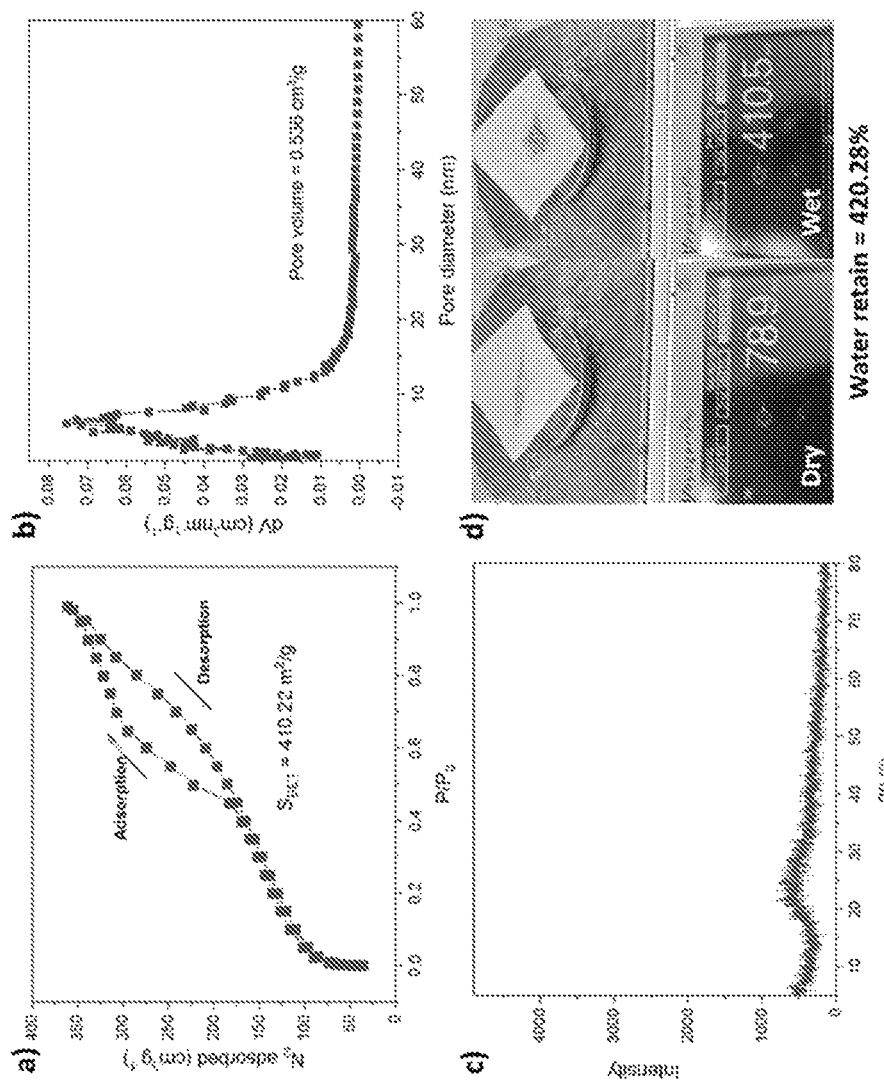
FIG. 14 shows physical characteristics of alkylated Nu-POC particles after MeI (6840 μg/mL: 98% MeI×15 μL) adsorption and detoxification (24 hours): a) $N_2$ adsorption/desorption isotherms at 77K. The $S_{BET}$ was calculated according to the $N_2$ adsorption isotherm at 77 K. b) Pore diameter distribution. c) PXRD results. d) Optical images of dried and water-saturated particles.
Figure 15:
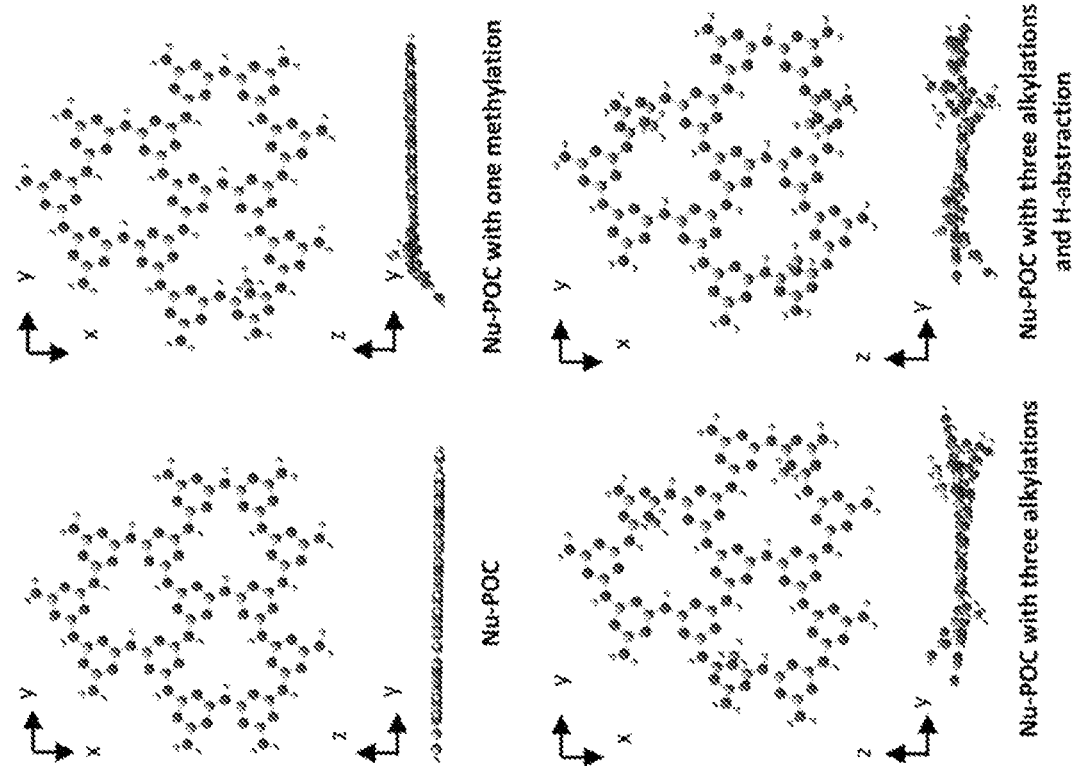
FIG. 15 shows Gaussian optimized structures of Nu-POC, alkylated Nu-POC analogs.
Figure 16:
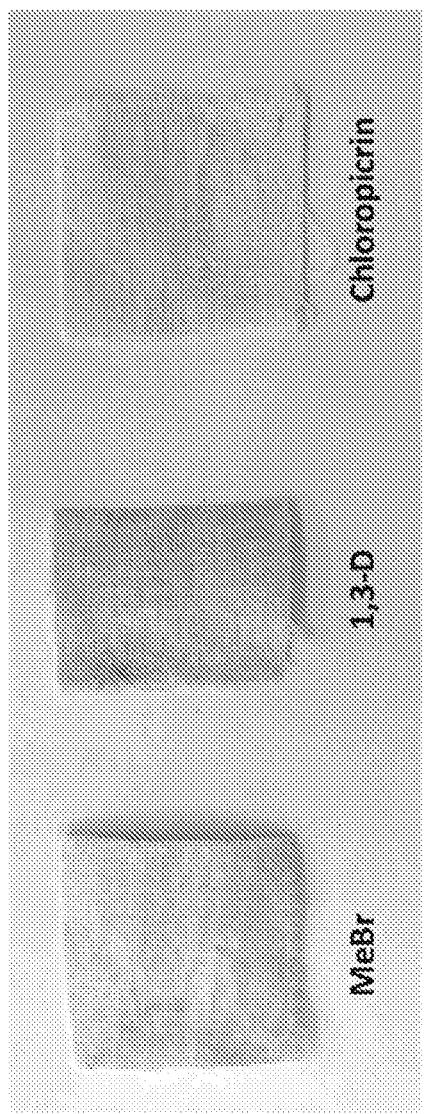
FIG. 16 shows optical images of POCotton after adsorption and detoxification of a) MeBr, b) 1,3-D, and c) chloropicrin. The different color intensity is highly related to the degree of the detoxification reaction that had happened, which determines the residual protective functions of the used POCotton

In certain aspects, interestingly, a color change of the POCotton from pale yellow to brown was noticed after MeI adsorption (concentration varied from 456 μg/mL to 4560 μg/mL) accompanied with a long-term storage (48 hours) (FIG. 2f), whose color intensities were correlated to the amount of MeI that has been adsorbed in the POCotton. Here, the color change is proposed as a result of the detoxification reaction of MeI by the Nu-POC (FIG. 2a and FIG. 13). According to the proposed reaction (FIG. 13), some nitrogen atoms in triazine rings inside the cage could be alkylated to quaternary ammonium salt structures:

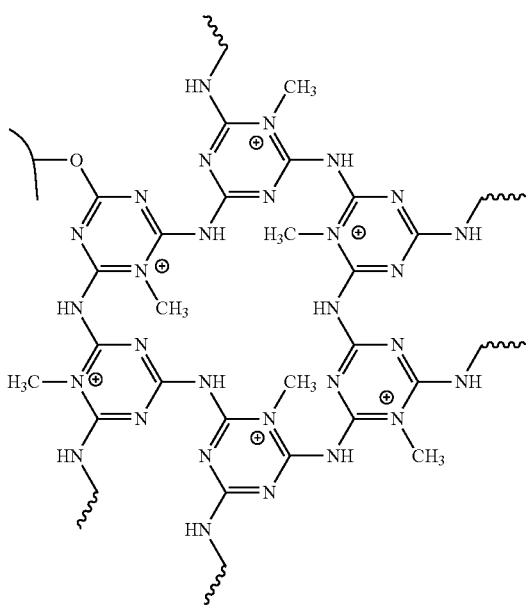

which can undergo elimination of hydroiodic acid (HI) to form a highly conjugated cage with a yellow color. However, the methyl groups inside the cage could reduce the space and surface area in the cage, and consequently reduce adsorption efficacy of the materials. The change of several tertiary triazine nitrogen structure in the cage will certainly hinder the nucleophilic alkylation reaction with MeI, impacting potential detoxification ability of the POCotton. The remaining adsorption efficacy of the colored POCotton samples (FIG. 2f) were exposed to 456 μg/mL of 98% MeI within 5 min again as a measurement of changes of the pore spaces and functions of the POCotton. The adsorption efficacy of the colored POCotton gradually decreased from 97.91% to 37.52% as increasing exposure levels of MeI, as well as with increased color intensities from pale yellow to dark brown (FIG. 2g). In addition, the BET surface area and the water regain of a colored Nu-POC (treated by 10 μL of 98% MeI and stored for 48-hours) decreased to 410.22 m²/g and 420.28%, respectively. Detailed results are available in FIGS. 14-15. The color change phenomenon of the POCotton was also noticed after the adsorption and detoxification of other alkylating fumigants including MeBr, 1,3-D, and chloropicrin (FIG. 16).

Figure 17:
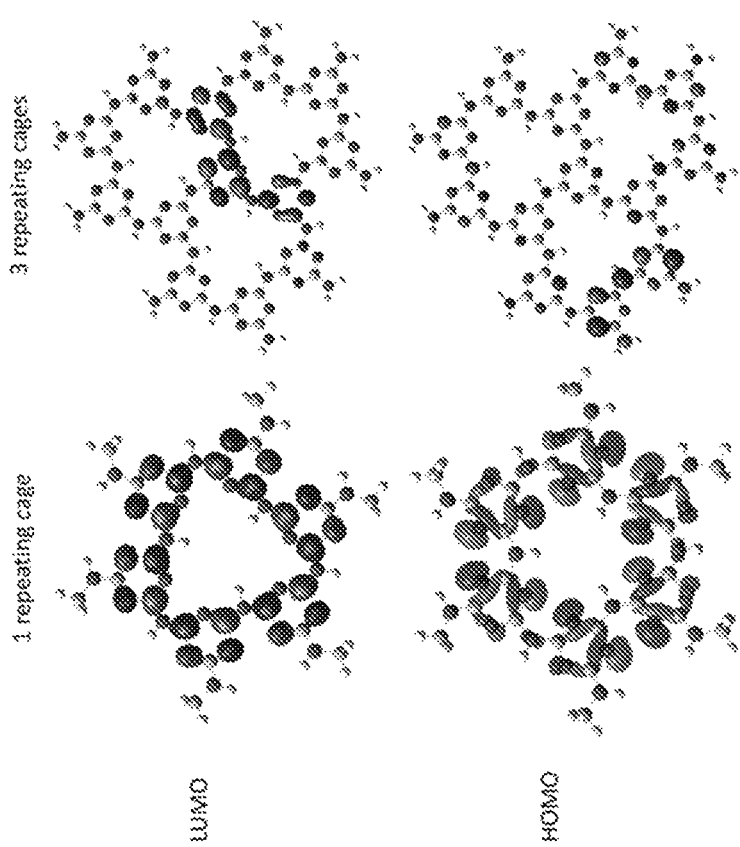
FIG. 17 shows the highest occupied molecular orbital (HOMO) and the lowest unoccupied molecular orbital (LUMO) of Nu-POC analog calculated based on density functional theory. The contribution of the lone pair electrons on the triazine-N to the HOMO of the Nu-POC analog indicates the potential reactivity of the triazine-N in detoxification of alkylating fumigants as a nucleophile.

In certain aspects, the triazine-N in the Nu-POC, where the highest occupied molecular orbital (HOMO) locates, was simulated as a nucleophile by Gaussian calculations (FIG. 17). After the alkylation of the triazine-N by MeI, a proton extraction from —NH— linkage by iodide led to the expansion of the conjugated system in the Nu-POC structure, causing the generation of a yellow color (FIG. 13). To fully understand the protective function of the Nu-POC, the structural changes of the Nu-POC were examined by storing the MeI-adsorbed Nu-POC (MeI-Nu-POC) for different durations.

Figure 3:
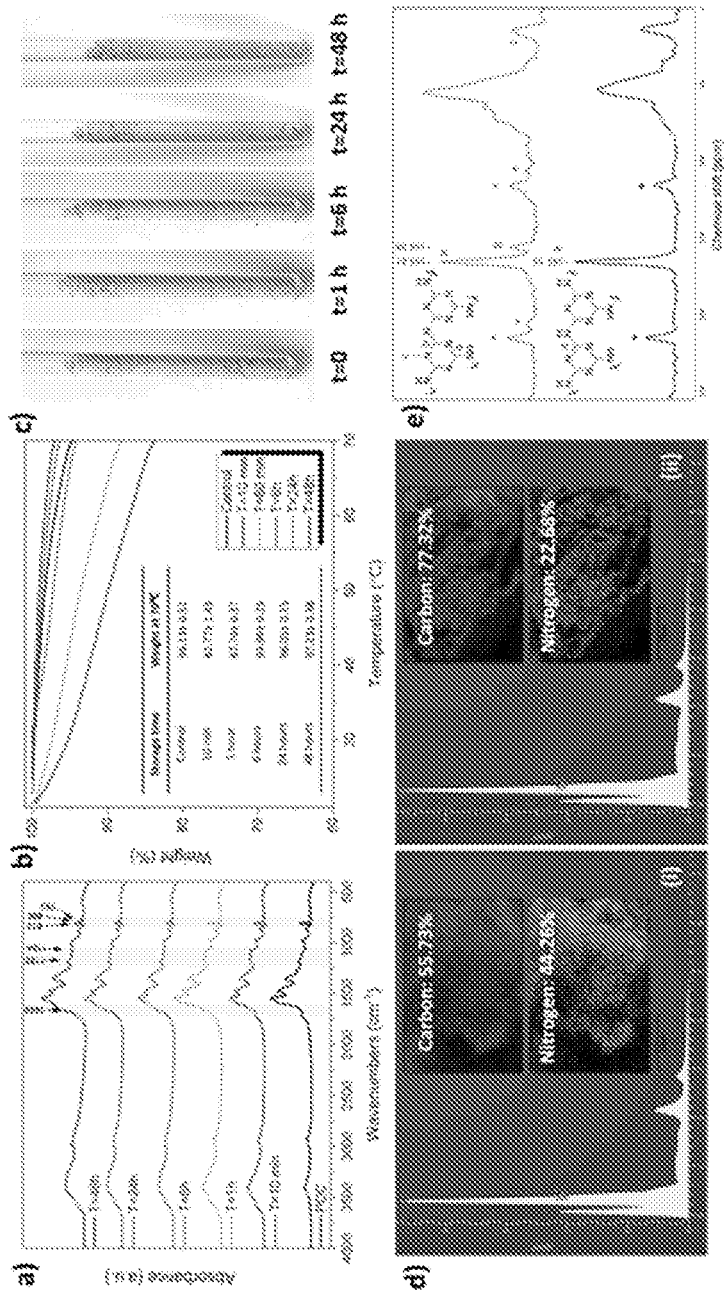
FIG. 3 shows an investigation of the fumigant removal and detoxification mechanisms of Nu-POC: a) FTIR spectra with different storage time. b) TGA curves with different storage time. c) Optical images of Nu-POC particles after MeI adsorption and different storage times. d) EDS spectra and color mappings of (i) Nu-POC, and (ii) MeI-Nu-POC after 24-hours storage. e) solid-phase $^{13}C$ CP/MAS NMR spectra: Nu-POC (black) and MeI-Nu-POC after 24-hours storage. The peaks labeled with * refer to the spinning sidebands.

In FIG. 3a, after short but sufficient adsorption of MeI (10 min), two new peaks at 1185 cm⁻¹ and 1104 cm⁻¹ emerged in the FTIR spectrum of MeI-Nu-POC, which refer to the presence of MeI in the sample[31]. With prolonging the adsorption time to 1 hour, no clear change was noticed in the spectra. However, the decrement of MeI and the generation of imine structures (1659 cm⁻¹) were shown after 6-hours storage. Moreover, the conversion of the amine linkage to imine linkage between triazine rings also resulted in a variation of the breathing mode of the triazine rings. New peaks at lower wavenumbers (800 cm⁻¹ and 782 cm⁻¹) were generated once the detoxification was achieved (FIG. 3a).

In certain aspects, the above phenomenon can also be noticed from thermogravimetric analysis (TGA), as shown in FIG. 3b. The weight losses of the MeI-Nu-POC under heating and N₂ flowing displayed different amounts of removable components in the materials after varied storage durations. MeI has occupied the mesopores of the Nu-POC during the initial adsorption process and such a status could stay same with short time adsorption and storage. Only 82.77% of its original weight remained when heated to 70° C. Moreover, the removable content gradually decreased by prolonging the storage time, and the data is summarized in the inserted table of FIG. 3b. Once the storage time reached 6 hours, the weight loss of the MeI-Nu-POC is comparable to the control group (i.e., the virgin Nu-POC). Meanwhile, the longer the storage time resulted in a darker color, indicating more intense detoxification reaction has happened in the MeI-Nu-POC (FIG. 3c). The EDS results indicate that, after MeI adsorption and storage (48 hours), the relative amount of carbon is 2.7 times higher than that of the nitrogen, whereas their contents were comparable in the virgin Nu-POC (FIG. 3d). More importantly, the chemical structure change of the MeI-Nu-POC after storage was further demonstrated by solid-phase ¹³C CP/MAS NMR (FIG. 3e). Compared with the virgin Nu-POC, a new peak at 156 ppm can be found in the MeI-Nu-POC spectrum, representing a new imine group in the structure. The broad peak showed at 53 ppm and 14 ppm (i.e., methylene and methyl groups, respectively) indicates the presence of Et₃N moieties, which terminated the Nu-POC growth by reacting with triazine chlorides. Although the new peak referring to methyl groups from MeI alkylation is hardly noticed, the EDS results proved its presence.

In certain aspects, the detoxification and colorimetric warning functions of the Nu-POC as well as the rapid adsorption of fumigants were fully understood. However, a relatively long time (e.g., >24 hours) is required to ensure the complete detoxification of fumigants in both the Nu-POC and the POCotton. After the long-term storage, a naked-eye readable signal can be generated to indicate the residual protective efficiency and to warn the expiration of protective functions of the POCotton. The colorimetric warning function of protective equipment is rarely reported yet crucial for achieving impeccable protection.

Figure 4:
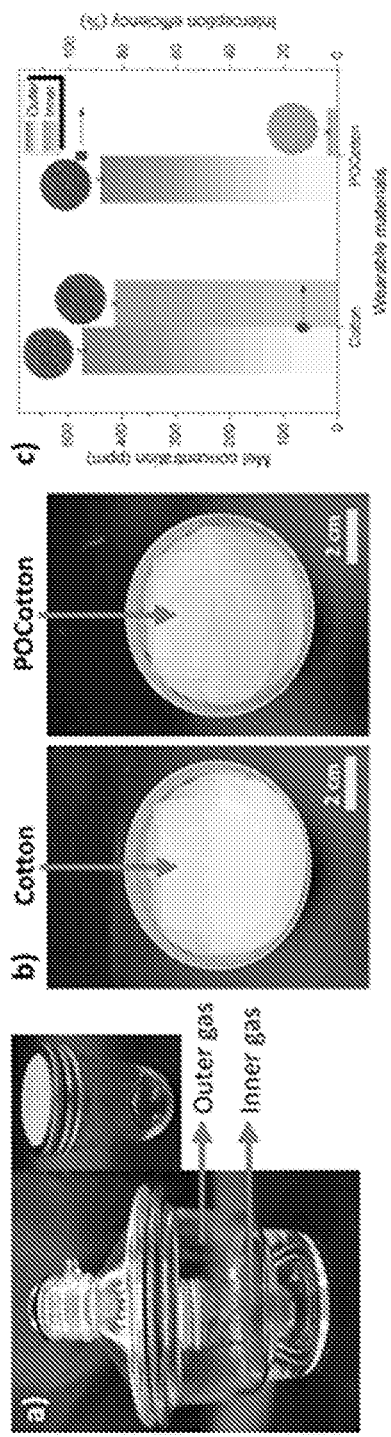
FIG. 4 shows a chemical protection demo by POCotton: a) Demo setups under passive diffusion. b) Two interception areas. A "sandwich" structure was formed: cotton-functional layer-cotton. c) MeI interception results under passive diffusion (10 min).

In certain aspects, the fumigant interception test was performed with the POCotton under passive diffusion, which helps to illustrate the merits of the POCotton in practical applications. As shown in FIG. 4a-b, kinetic MeI adsorption functions of the POCotton were evaluated according to the amount of MeI that can pass through the fabric as a filter from the outer chamber to the inner one. In FIG. 4c, the concentration of MeI in the outer and inner chambers was monitored with a paper-based colorimetric sensor (see details in FIG. 18).[32] Traditional cotton fabric shows a negligible protective function by showing a 12.7% decrement of MeI concentration between the two chambers. Nevertheless, the POCotton presents an outstanding interception of MeI through passive diffusion. The concentration difference between the two chambers dramatically increased to 411 ppm, indicating 95.6% of the MeI in the outer chamber has been adsorbed by the POCotton (FIG. 4c).

In certain aspects, we have successfully grown highly porous triazine-based Nu-POC on surfaces of cotton fibers via a novel in-situ synthesis process, achieving super-adsorptive and wearable POCotton for efficient fumigant adsorption and detoxification. The prepared POCotton successfully retains the ultrahigh specific surface area and the porosity of the Nu-POC as well as the wear ability and serviceability of cotton fibers. The POCotton shows rapid (i.e., reached equilibrium in 1 min) and massive capacity (i.e., 596.88 mg/g of Nu-POC) of fumigant adsorption, which is attributed to the capillary condensation of the vaporous toxicant in its mesoporous structure. More importantly, the nucleophilicity of the Nu-POC structure and its alkylation reaction with carcinogenic fumigants (e.g., MeI) has led to complete detoxification of the fumigant and coloration of the resulted fabric subsequently. Such a mechanism was proven experimentally and theoretically. The detoxification of fumigants by the Nu-POC resulted in a distinct color change of the material, providing signals of the failure of the protective function and the replacement of the POCotton during practical applications. This work illustrated the prospect of the advanced wearable POCs in the development of protective equipment, functional household apparels, and novel filters for fumigants as well as other toxic organic vapors.

II. Examples

In-Situ Synthesis of Nu-POC on Cotton Cellulose (POCotton): Firstly, cotton fabrics (5 cm×5 cm, 2 pieces) were activated by reacting with cyanuric chloride (CCl) in DMAc at 0° C. for 1 hour. The CCl solution was prepared by dissolving CCl (4.5 mmol) in 60 mL DMAc with 1 mL of triethylamine ($Et_3N$). Secondly, the CCl-activated cotton fabrics were transferred into 90 mL of DMSO containing melamine (5.6 mmol) and 1 mL $Et_3N$ in a 250 mL round-bottom flask. Then, 30 mL of additional CCl (2.8 mmol) in DMSO was added into the flask dropwise under stirring and $N_2$ gas purging (20 min). The reaction system was well-sealed and heated to 150° C. within 60 min and kept stirring at 500 rpm for 24 hours. The as-obtained POCotton was washed with DMSO, deionized water and methanol after cooling the system back to room temperature. The POCotton was dried under vacuum at room temperature. The grafting ratio (%) was calculated based on weight add-on, according to Equation 1.

$$\text{Grafting ratio (\%)} = \frac{W_{POCotton} - W_{Cotton}}{W_{Cotton}} \times 100\% \quad (1)$$

Where $W_{Cotton}$ and $W_{POCotton}$ refer to the weights of cotton fabrics before and after the in-situ synthesis of POC, respectively.

Figure 19:
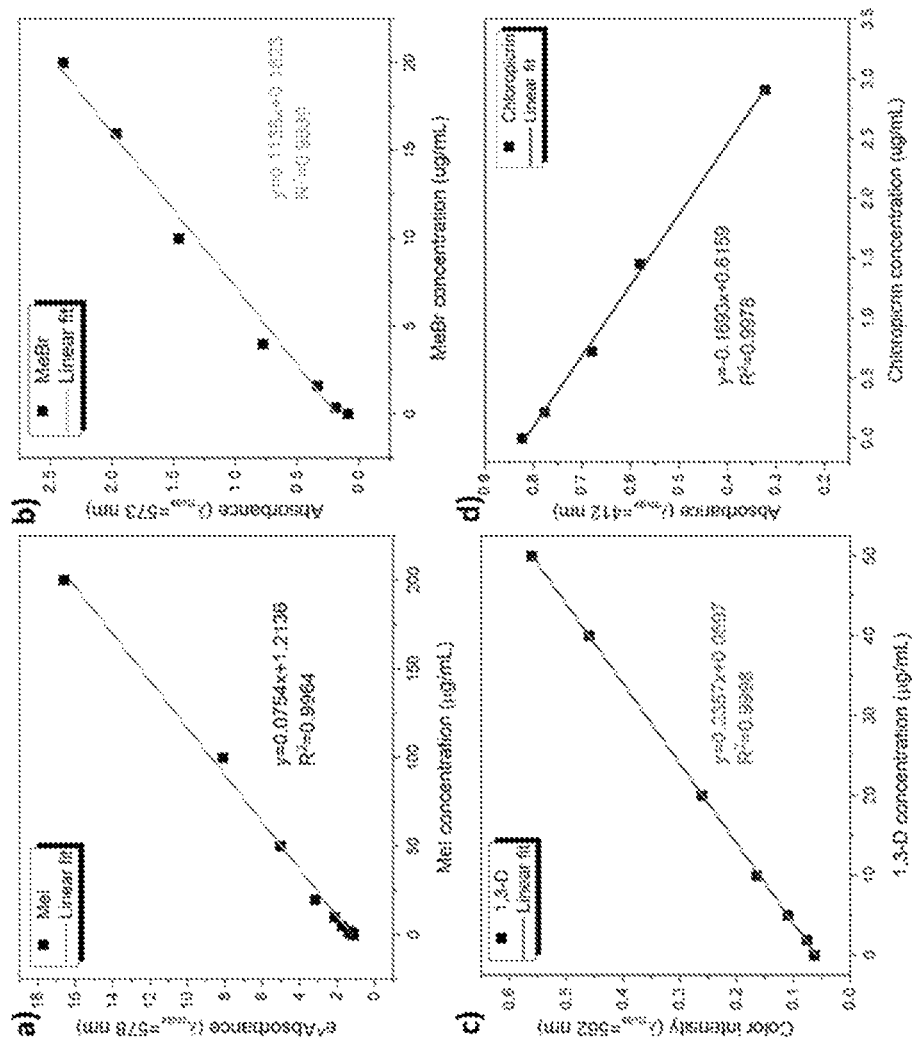
FIG. 19 shows calibration curves of the color intensity correlated to different concentration of fumigants: a) MeI, b) MeBr, c) 1,3-D, and d) chloropicrin.

Colorimetric Evaluation of Fumigant Adsorption: The evaluations of fumigant removal by specific materials were performed according to our previous study.[18] Taking MeI detection as an example, a known amount of adsorbent was sealed in a 5 mL glass vial capped with PTFE/silicone septum. A calculated amount of fumigant solution was injected into the vial with a gas-tight syringe. After different incubation time, 2 mL of headspace gas was pumped out with a 5 mL gas-tight syringe and injected into 1 mL of DMF containing 4-(p-nitrobenzyl)pyridine (NBP) (20 wt %). The NBP/DMF solution was incubated at room temperature for 10 min in order to show a blue color by reacting with MeI through a nucleophilic substitution reaction, whose intensity is corresponding to the residual concentration of MeI in the vial. The color intensity was monitored with a UV-vis spectrophotometer at the maximum absorption wavelength ($\lambda_{max}$=578 nm) with appropriate dilution with DMF. The residual concentration of fumigants after adsorption was obtained from the established calibration curves (FIG. 19). The fumigant removal (%) was calculated based on the concentration (µg/mL of DMF) change after different adsorption times, and the equation is shown as Equation 2.

$$\text{Fumigant removal (\%)} = \frac{C_0 - C_t}{C_0} \times 100\% \quad (2)$$

Where, $C_0$ and $C_t$ refer to fumigant concentrations in the headspace of the vial after adsorption without and with specific adsorbent, respectively.

The removal of MeBr and 1,3-D was performed through similar procedures as that of MeI with some modifications. The removal of chloropicrin was quantified via a cysteine-Ellman's reagent detection system.[33]

Chemicals and Materials

Cyanuric chloride (CCl) (99%), melamine (99%), N,N'-dimethyl formacetamine (DMAc) (HPLC grade), dimethyl sulfoxide (DMSO) (HPLC grade, 99.7%), and triethylamine (99.8%) ($Et_3N$) were purchased from Sigma-Aldrich (St Louis, MO, USA). Desized and bleached cotton fabric Style 400 was purchased from TestFabrics Inc. (West Pittston, PA, USA).

Synthesis of Nucleophilic Porous Organic Cage (Nu-POC) from Cyanuric Chloride and Melamine Cyanuric chloride (7.5 mmol) was dissolved in 75 mL N,N'-dimethyl sulfoxide (DMSO) (Solution 1). Then, Solution 1 was added dropwise into Solution 2, which was prepared by dissolving melamine (7.5 mmol) in 75 mL DMSO in a 250 mL round-bottom flask. And 1 mL of triethylamine ($Et_3N$) was added into the system. During the mixing of Solutions 1 and 2, nitrogen gas was continuously purged into the reaction system for 20 min. After that, the flask was sealed with a glass stopper and gradually heated to 150° C. within 60 min. The reaction system was heated at 150° C. for 24 hours. The resultant egg-white precipitates were filtrated after cooling the system to room temperature and were thoroughly washed with excess amount of DMSO, deionized water, and methanol, and were dried under vacuum at room temperature. The yield was weighted as 79.8%.

Synthesis of Nonporous $N^2,N^{2'},N^{2''}$-(1,3,5-Triazine-2,4,6-triyl)tris(1,3,5-triazine-2,4,6-triamine) (1CCl-3M)

The molar ratio of CCl/melamine was controlled as ⅓ in this case. Melamine (7.5 mmol) and CCl (2.5 mmol) were dissolved in 75 mL DMSO separately. $Et_3N$ (1 mL) was added in melamine/DMSO solution. The melamine and CCl were mixed dropwise in a 250 mL round-bottom flask. The reaction system was purged with $N_2$ for 20 min before sealing the flask with a glass stopper. According to the temperature-dependent reactivity of three triazine-chlorides in CCl,[34] the reaction system was firstly stirred at 0° C. for 1 hour. Then, the system was transferred to room temperature (25° C.) and stirred for an extra 2 hours. Finally, the system was heated to 80° C. and reacted for another 21 hours. The white precipitates were filtrated with filter paper and washed with excess amount of DMSO, deionized water, and methanol. The particles were dried under vacuum at room temperature (yield=48.5%). The resultant particle was structurally characterized with FTIR, whose major peaks are shown at 3393 cm$^{-1}$ ($v_{(1° N-H)}$), 3230 cm$^{-1}$ ($v_{(2° N-H)}$), 1735 cm$^{-1}$ and 1661 cm$^{-1}$ ($v_{(C=N)}$), 1536 cm$^{-1}$ and 1447 cm$^{-1}$ (triazine ring), and 770 cm$^{-1}$ ($\omega_{(triazine\ ring)}$).

Water Regain Test

Specific particles (~100 mg) were dispersed in 10 mL deionized water and vigorously stirred for 1 hour. Then the suspension was filtered with Whatman filter paper (Grade 1, Cat. No.: 1001 110). The water on the precipitate surface was wiped out with another filter paper. The weight of the compound after water adsorption was measured for calculating the water regain (%) according to Equation 51.

$$\text{Water retain (\%)} = \frac{W_{Wet} - W_{Dry}}{W_{Dry}} \times 100\% \qquad (S1)$$

Where $W_{Wet}$ refers to the weight of compounds after water adsorption. $W_{Dry}$ refers to the dry weight of the compound, which was measured after drying the filtrated wet particle in an oven (60° C.).

Characterizations

Fourier-transform infrared (FTIR) analysis of materials were performed on a Nicolet 6700 spectroscopy (Thermo Electron Co., MA, USA). The scanning range was 400-4000 cm$^{-1}$ with 2 cm$^{-1}$ resolution. Scanning electron microscope (SEM) images were obtained from Quattro environmental scanning electron microscope (Thermo Fischer Scientific, USA). Energy-dispersive X-ray spectroscopy (EDS) was accessed with Scios SEM/focused ion beam microscope (Thermo Fischer Scientific, USA). Thermalgravimetric analysis (TGA) was examined with a TG-60 system (Shimadzu USA). The sample was firstly heated to 120° C. (10° C./min) and hold for 2 min in order to eliminate any free water. Then, the sample was cooled to room temperature under N$_2$ flow (30 mL/min) and reheated to 600° C. On the other hand, for the examination of adsorption and detoxification of MeI, the sample was heated from room temperature to 70° C. (20° C./min) under fast N$_2$ flow (200 mL/min). Powder X-ray diffraction (PXRD) measurements were investigated using a D/max-2550 PC (Geigerflex, Rigaku, Japan) with Cu-Kα radiation (λ=1.5406 Å)). N$_2$ adsorption-desorption isotherms were obtained from a physisorption system of ASAP 2020 (Micromeritics Co., USA). The samples were de-gassed at 60° C. for 1 hour before testing. The BET surface area and porous structures were calculated according to Brunauer-Emmett-Teller (BET) and Horvath-Kawazoe (HK) theory models, respectively. Solid phase $^{13}$C CP/MAS NMR was carried out using a Bruker Avance 400 spectrometer. Air permeability was measured according to ASTM D 737 method using an air permeability tester (Frazier Precision Instrument Company, Inc., MD, USA). Tensile strength was characterized based on ASTM D 5035-06 method using an Instron 5566 tester (Instron Co., MA, USA).

Fumigant Adsorption Evaluations

Methyl Bromide (MeBr)

POCotton (100 mg) was sealed in a 5 mL glass vial capped with PTFE/silicone septum. MeBr solution (10 µL×2 mg/mL in methanol) was injected into the vial with a gas-tight syringe. After different incubation times, 2 mL of headspace gas was pumped out with a 5 mL gas-tight syringe and injected into 1 mL of DMF containing 4-(p-nitrobenzyl)pyridine (NBP) (20 wt %). The NBP/DMF solution was incubated at 70° C. for 5 min in order to show a blue color by reacting with MeBr through an alkylation reaction, whose intensity is correlated to the residual concentration of MeBr in the vial. The color intensity was monitored with a UV-vis spectrophotometer at the maximum adsorption wavelength of $\lambda_{max}$=573 nm. The residual concentration of MeBr after adsorption can be calculated according to an established calibration curve (FIG. 19b).

1,3-Dichloroproene (1.3-D)

POCotton (100 mg) was sealed in a 5 mL glass vial capped with PTFE/silicone septum. 1,3-D solution (8 µL×5 mg/mL in methanol) was injected into the vial with a gas-tight syringe. After different incubation times, 5 mL of headspace gas was pumped out with a 5 mL gas-tight syringe and injected into 1 mL of DMF containing 4-(p-nitrobenzyl)pyridine (NBP) (20 wt %). The NBP/DMF solution was incubated at 70° C. for 10 min in order to show a blue color by reacting with 1,3-D through an alkylation reaction, whose intensity is corresponding to the residual concentration of 1,3-D in the vial. The color intensity was monitored with a UV-vis spectrophotometer at the maximum adsorption wavelength ($\lambda_{max}$=562 nm). The residual concentration of 1,3-D after adsorption was measured based on an established calibration curve (FIG. 15c).

Chloropicrin

POCotton (100 mg) was sealed in a 5 mL glass vial capped with PTFE/silicone septum. Chloropicrin solution (5 µL×1 mg/mL in methanol) was injected into the vial with a gas-tight syringe. After different incubation times, 2 mL of headspace gas was pumped out with a 5 mL gas-tight syringe and injected into a standard cysteine solution, contained 2.5 mL monobasic sodium phosphate buffer (pH=8.0) and 250 µL 0.5 mM cysteine. The system was incubated at room temperature for 15 min to allow the reaction between residual chloropicrin and the sulfhydryl group of cysteine. [35] Then, 50 µL of Ellman's reagent (4 mg/mL) was added to colorimetrically measure the chloropicrin concentration by the UV-vis spectrophotometer at the maximum adsorption wavelength ($\lambda_{max}$=412 nm), which is negatively correlated to the color intensity that generated from the reaction between Ellman's reagent and cysteine (FIG. 19d).

Paper-Based Colorimetric Detection Procedures

Figure 18:
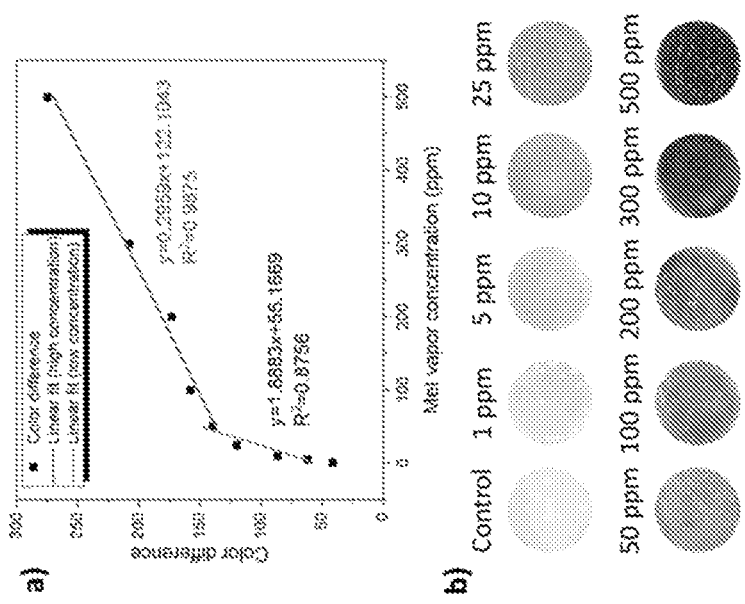
FIG. 18 shows a) The calibration curve for quantification of MeI concentration according to color intensity (i.e., color difference). b) The optical images of paper-based colorimetric sensor after detecting corresponding concentration of MeI.

The colorimetric sensing solution was prepared by dissolving NBP (20 wt %) in DMF. Then, 100 µL of the sensing solution was dropped on a glass microfiber filter paper (diameter=1 cm) for detection of MeI concentration in a gas chamber. The color of the sensor was read by a software of ColorAssist in a smart phone, and the color change after MeI detection was calculated according to Equation S2. The color difference was correlated to the concentration of MeI in the gas chamber (FIG. 18).

$$\text{Color difference} = \sqrt[2]{(R_1 - R_0)^2 + (G_1 - G_0)^2 + (B_1 - B_0)^2} \qquad (S2)$$

Where R, G, and B are the values of red, green, and blue channels of RGB color system, respectively. The subscripts of 0 and 1 refer to the samples before and after the MeI detection, respectively.

Time-Dependent Synthesis of POCotton

Structurally speaking, as presented in FIG. 5a, the characteristic peaks of CCl and melamine appeared in the spectrum of material obtained after 2-hours reaction. However, a sharp peak at 850 cm$^{-1}$ disappeared, referring to the consumption of triazine chlorides in CCl. Moreover, comparing with the spectrum of melamine, peaks at 3100-3600 cm$^{-1}$ shifted to lower wavenumbers, illustrating the interaction (e.g., aggregation) between CCl and melamine and mostly related to the changes of the primary amines in melamine. The FTIR spectra started to change significantly once the reaction time reached 6 hours, and no obvious difference was found by prolonging the reaction time (e.g., 24 or 48 hours). The peak change is mostly related to the disappearance of the characteristic peaks of primary amines (3394 cm$^{-1}$, 2697-2541 cm$^{-1}$, 1736 cm$^{-1}$, and 1662 cm$^{-1}$), [36] which demonstrated the occurrence of the condensation reaction between melamine and CCl. More importantly, once the reaction time reached 6 hours, the characteristic peaks of triazine ring (i.e., the stretching and bending of C=N and C—N bonds) merged and became broader (1549-1552 cm$^{-1}$, 1474-1479 cm$^{-1}$, 1352-1354 cm$^{-1}$).[37] A sharp peak at 813 cm$^{-1}$, which corresponds to the breathing mode of the triazine ring in the Nu-POC structure, can be observed in the spectra of the products synthesized with longer reaction times (>6 hours).

The morphology of the Nu-POC on cotton fibers is distinguishable according to synthesis time (FIG. 5b): 1) CCl and melamine form large aggregates on the fiber surface (2-hours reaction); 2) nanosized and molecular-sized aggregates covered on the fiber surfaces (6-hours reaction); 3) construction and achievement of uniform particles with mesopores on the fiber surfaces (>24 hours reaction). It is important to note that both Nu-POC and POCotton can only perform fumigant removal efficacy when the mesoporous structures are achieved. The increase of the Nu-POC content on the POCotton is observed when the synthesis time increased from 6 hours to 24 hours, and no further changes were noticed in the 48-hours sample. This phenomenon is consistent with the FTIR spectra as the peak intensities of the Nu-POC is relatively low when the synthesis time was only 6 hours. However, the 48-hours synthesis could result in over-oxidation and severe mechanical strength loss of the resultant POCotton.

Characterization of Nu-POC after MeI Adsorption and Detoxification

Experimental Analysis

A serial of tests was performed to gain an insight view into the physical characteristic changes of the Nu-POC after MeI adsorption and storage detoxification (Me-Nu-POC). As shown in FIG. 14a, the N$_2$ adsorption-desorption isotherm of Me-Nu-POC showcased the type IV adsorption with a hysteresis under high partial pressure (P/P$_0$=0.4-1.0). Compared with the brand-new Nu-POC (FIG. 6a), its BET surface area decreased to 410.22 m$^2$/g. Meanwhile, as presented in FIG. 14b, the pore diameter distribution did not change significantly, while a loss of the pore volume from 0.740 cm$^3$/g to 0.536 cm$^3$/g was measured. In addition, the PXRD of the Me-Nu-POC was further examined, shown in FIG. 14c. The broad peak at 2θ=20° shifted to around 25° represents a change of the molecular arrangement after the alkylation of the Nu-POC by MeI. The porosity decrease of the Me-Nu-POC was expressed by the 44.0% decrease of the water regain of alkylated-Nu-POC (420.28%) to that of the Nu-POC (750.67%). Interestingly, this phenomenon is highly correlated to the MeI removal property of the alkylated-Nu-POC, whose efficiency dropped by 52.2% compared with the virgin Nu-POC (FIG. 11). This phenomenon further indicates that the fumigant removal by the Nu-POC relies more on its mesopores, where fumigant molecules can be sequestered.

Computational Analysis

Density functional theory was applied to simulate the structure change of the Nu-POC before and after MeI adsorption and detoxification. As presented in FIG. 15, the geometry optimization of the Nu-POC analog with three repeating cages and its alkylated products were performed on the Gaussian 09 program under the B3LYP/3-61G (d,p) level of theory in vacuum condition. The Nu-POC shows a planer geometry, allowing the pile-up and alignment of the polymer, which achieved the high specific surface area and massive porosity. However, the alkylation of the Nu-POC by MeI or other fumigants disordered the planarity of the Nu-POC by showing a bended geometry. The bending is caused by the steric hindrance brought from the replacement of the lone pair electrons on triazine-N to a methyl group from MeI. The disturbance of the planar geometry had been enhanced when more alkylation reactions have happened (FIG. 15). The loss of the planarity of the alkylated Nu-POC could suppress the molecular alignment, resulting in the decrease of specific surface area as well as the porosity of the alkylated Nu-POC.

III. References

[1] R. P. Schwarzenbach, B. I. Escher, K. Fenner, T. B. Hofstetter, C. A. Johnson, U. Von Gunten, B. Wehrli, Science 2006, 313, 1072.
[2] B. Ham, Science 2019, 366, 1084.
[3] S. Loganathan, T. Murugan, in Sustain. Agric. Towar. Food Secur., 2017, pp. 359-373.
[4] G. Shen, D. J. Ashworth, J. Gan, S. R. Yates, Environ. Sci. Technol. 2016, 50, 1182.
[5] L. Joseph, B. M. Jun, M. Jang, C. M. Park, J. C. Muñoz-Senmache, A. J. Hernández-Maldonado, A. Heyden, M. Yu, Y. Yoon, Chem. Eng. J. 2019, 369, 928.
[6] H. Fan, J. Gu, H. Meng, A. Knebel, J. Caro, Angew. Chemie-Int. Ed. 2018, 57, 4083.
[7] A. Alsbaiee, B. J. Smith, L. Xiao, Y. Ling, D. E. Helbling, W. R. Dichtel, Nature 2016, 529, 190.
[8] Y. Liu, Y. Ma, J. Yang, C. S. Diercks, N. Tamura, F. Jin, O. M. Yaghi, J. Am. Chem. Soc. 2018, 140, 16015.
[9] Y. Zeng, R. Zou, Y. Zhao, Adv. Mater. 2016, 28, 2855.
[10] S. Kandambeth, B. P. Biswal, H. D. Chaudhari, K. C. Rout, S. Kunjattu H., S. Mitra, S. Karak, A. Das, R. Mukherjee, U. K. Kharul, R. Banerjee, Adv. Mater. 2017, 29, 1603945.
[11] M. A. Khayum, V. Vijayakumar, S. Karak, S. Kandambeth, M. Bhadra, K. Suresh, N. Acharambath, S. Kurungot, R. Banerjee, ACS Appl. Mater. Interfaces 2018, 10, 28139.
[12] R. K. Yadav, A. Kumar, N. J. Park, K. J. Kong, J. O. Baeg, J Mater. Chem. A 2016, 4, 9413.
[13] D. M. Alzate-Sánchez, B. J. Smith, A. Alsbaiee, J. P. Hinestroza, W. R. Dichtel, Chem. Mater. 2016, 28, 8340.
[14] Y. Liu, Y. Ma, Y. Zhao, X. Sun, F. Gindara, H. Furukawa, Z. Liu, H. Zhu, C. Zhu, K. Suenaga, P. Oleynikov, A. S. Alshammari, X. Zhang, O. Terasaki, O. M. Yaghi, Science 2016, 351, 365.
[15] L. O. Ruzo, Pest Manag. Sci. 2006, 62, 99.
[16] Travel Weekly, http://www.travelweekly.co.uk/articles/310709/egypt-hotel-death-couple-slept-next-to-recently-fumigated-room (accessed: September 2018).

[17] CNN. https://www.cnn.com/2015/09/10/us/virgin-islands-pesticide-investigation/index.html (accessed: September 2015).
[18] P. Tang, M. Zhang, B. Ji, T. Yong, G. Sun, *Adv. Funct. Mater.* 2019, 29, 1905990.
[19] Y. Zhang, Y. Zhang, X. Wang, J. Yu, B. Ding, *ACS Appl. Mater. Interfaces* 2018, 10, 34802.
[20] A. X. Lu, M. McEntee, M. A. Browe, M. G. Hall, J. B. Decoste, G. W. Peterson, *ACS Appl. Mater. Interfaces* 2017, 9, 13632.
[21] Y. Bian, R. Wang, S. Wang, C. Yao, W. Ren, C. Chen, L. Zhang, *J. Mater. Chem. A* 2018, 6, 15807.
[22] L. A. Meyer, United States Department of Agricultural https://www.ers.usda.gov/webdocs/publications/98040/cws-20c.pdf?v=5145.4 (accessed: March 2020)
[23] H. A. Patel, F. Karadas, A. Canlier, J. Park, E. Deniz, Y. Jung, M. Atilhan, C. T. Yavuz, *J Mater. Chem.* 2012, 22, 8431.
[24] W. Wang, Y. Yuan, F. X. Sun, G. S. Zhu, *Chinese Chem. Lett.* 2014, 25, 1407.
[25] R. Xue, H. Guo, T. Wang, X. Wang, J. Ai, L. Yue, Y. Wei, W. Yang, *Mater. Lett.* 2017, 209, 171.
[26] S. K. Kundu, A. Bhaumik, *RSC Adv.* 2015, 5, 32730.
[27] P. Wen, C. Zhang, Z. Yang, R. Dong, D. Wang, M. Fan, J. Wang, *Tribol. Int.* 2017, 111, 57.
[28] H. Zhao, J. H. Kwak, Z. Conrad Zhang, H. M. Brown, B. W. Arey, J. E. Holladay, *Carbohydr. Polym.* 2007, 68, 235.
[29] S. Xie, X. Liu, B. Zhang, H. Ma, C. Ling, M. Yu, L. Li, J. Li, *J Mater. Chem.* A 2015, 3, 2552.
[30] M. Gorji, M. Karimi, S. Nasheroahkam, *J Ind. Text.* 2018, 47, 1166.
[31] A. Chowdhury, S. T. Thynell, *Thermochim. Acta* 2006, 443, 159.
[32] P. Tang, H. T. Leung, G. Sun, *Anal. Chem.* 2018, 90, 14593.
[33] P. Tang, H. T. Leung, M. T. Gomez, G. Sun, *ACS Sensors* 2018, 3, 858.
[34] H. A. Patel, F. Karadas, A. Canlier, J. Park, E. Deniz, Y. Jung, M. Atilhan, C. T. Yavuz, *J. Mater. Chem.* 2012, 22, 8431.
[35] P. Tang, H. T. Leung, M. T. Gomez, G. Sun, *ACS Sensors* 2018, 3, 858.
[36] V. Sangeetha, N. Kanagathara, R. Sumathi, N. Sivakumar, G. Anbalagan, *J Mater.* 2013, 2013, 1.
[37] R. Xue, H. Guo, T. Wang, X. Wang, J. Ai, L. Yue, Y. Wei, W. Yang, *Mater. Lett.* 2017, 209, 171.x All publications, patents and patent applications cited in this specification are herein incorporated by reference as if each individual publication, patent or patent application were specifically and individually indicated to be incorporated by reference. Although the foregoing disclosure has been described in some detail by way of illustration and example for purposes of clarity of understanding, it will be readily apparent to those of ordinary skill in the art that, in light of the teachings of this application, that certain changes and modifications may be made thereto without departing from the spirit or scope of the appended claims.

What is claimed is:

1. A method for detoxifying and/or removing a fumigant vapor from an environment, the method comprising:
   contacting the fumigant vapor with a triazine-based nucleophilic porous organic cage grafted on a cotton fiber (POCotton), comprising:
   a six-membered triazine ring cage grafted to a cotton fiber according to formula I:

wherein each § represents attachment to another triazine ring cage, a cotton fiber, $NH_2$ or H;

and wherein each § represents between 0 and 30 triazine ring cages before termination, to allow the detoxification or removal of the fumigant vapor.

2. The method of claim 1, wherein the fumigant vapor is a member selected from the group consisting of hydrogen cyanide, naphthalene, nicotine, methyl iodide, methyl bromide, dichloropropene, propylene oxide, dibromochloropropane, organophosphate insecticides, and chloropicrin.

3. The method of claim 1, wherein the fumigant vapor is a member selected from the group consisting of methyl iodide (MeI) and methyl bromide (MeBr).

4. The method of claim 1, wherein the fumigant vapor is sequestered by the six-membered triazine ring cage grafted to a cotton fiber.

5. The method of claim 4, wherein the fumigant vapor is sequestered by the six-membered triazine ring cage grafted to a cotton fiber with a concomitant color change.

6. A method of incorporating novel functional agents into a POCotton-triazine-based nucleophilic porous organic cage grafted on a cotton fiber, comprising:
   providing a six-membered triazine ring cage grafted to a cotton fiber according to formula I:

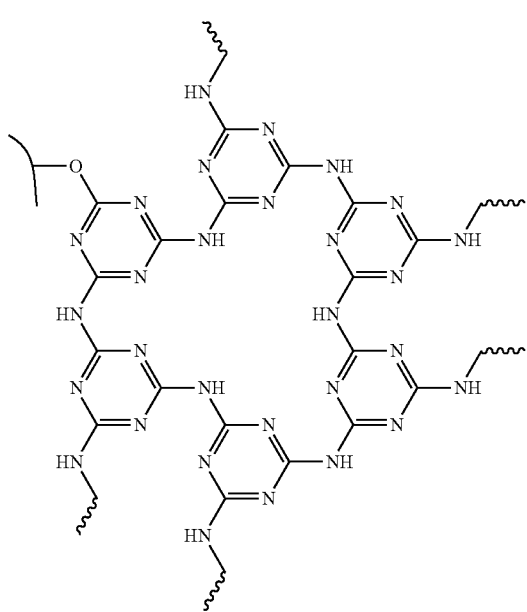

wherein each ⅊ represents attachment to another triazine ring cage, a cotton fiber, $NH_2$, or H;

wherein each ⅊ represents between 0 and 30 triazine ring cages before termination; and contacting the six-membered triazine ring cage grafted to a cotton fiber with a functional agent to thereby incorporate the functional agent.

7. The method of claim 6, wherein the functional agent is a member selected from the group consisting of a photosensitizer, a color indicator, and a reactive agent.

8. The method of claim 7, wherein the photosensitizer is a member selected from the group consisting of Rose Bengal, sodium 2-anthroquinone sulfate, anthroquinone-2-carboxylic acid, menadione sodium bisulfite, and riboflavin 5-sulfate.

9. The method of claim 7, wherein the color indicator is a member selected from the group consisting of phenol red, phenolphthalein, bromophenol blue, alizarin yellow R, and p-(4-nitrobenzyl)pyridine.

* * * * *